US009243288B2

(12) United States Patent
Ness et al.

(10) Patent No.: US 9,243,288 B2
(45) Date of Patent: Jan. 26, 2016

(54) CARTRIDGE WITH LYSIS CHAMBER AND DROPLET GENERATOR

(75) Inventors: Kevin Dean Ness, Pleasanton, CA (US);
Samuel Burd, Oakland, CA (US);
Benjamin Joseph Hindson, Livermore, CA (US); Phillip Belgrader, Severna Park, MD (US); Billy W. Colston, Jr., San Ramon, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 450 days.

(21) Appl. No.: 13/250,815

(22) Filed: Sep. 30, 2011

(65) Prior Publication Data
US 2012/0028311 A1 Feb. 2, 2012

Related U.S. Application Data

(63) Continuation of application No. 12/586,626, filed on Sep. 23, 2009, now Pat. No. 9,156,010.

(60) Provisional application No. 61/194,043, filed on Sep. 23, 2008, provisional application No. 61/206,975, (Continued)

(51) Int. Cl.
*C12Q 1/68* (2006.01)
*C12M 3/00* (2006.01)
(Continued)

(52) U.S. Cl.
CPC .............. *C12Q 1/686* (2013.01); *B01F 3/0807* (2013.01); *B01F 13/0062* (2013.01); *B01L 3/0241* (2013.01); *B01L 3/502784* (2013.01); *G01N 21/3563* (2013.01); *G01N 21/6428* (2013.01); *G01N 21/6486* (2013.01); *B01L 7/52* (2013.01); *B01L 7/525* (2013.01);
(Continued)

(58) Field of Classification Search
CPC .. B01F 3/0807; B01F 13/0062; B01L 3/0241; B01L 3/502784; B01L 7/52; B01L 7/525; B01L 2300/0816; B01L 2300/0819; B01L 2300/1822; B01L 2400/0478; B01L 2400/0487; B01L 2400/0622; B01L 2400/0689; G01N 21/3563
USPC .................................. 435/91.2, 287.2, 294.1
See application file for complete search history.

(56) References Cited

U.S. PATENT DOCUMENTS 3,575,220 A 4/1971 Davis et al.
4,051,025 A 9/1977 Ito
(Continued)

FOREIGN PATENT DOCUMENTS

EP 1 522 582 A2 4/2005
EP 1 522 582 B1 4/2007
(Continued)

OTHER PUBLICATIONS

Young, Lee W., Authorized officer, International Searching Authority, International Search Report, PCT Application Serial No. PCT/US2009/05317; search date: Nov. 20, 2009.
(Continued)

*Primary Examiner* — Michael Hobbs
(74) *Attorney, Agent, or Firm* — Kolisch Hartwell, P.C.

(57) ABSTRACT

Systems, including apparatus, methods, compositions, kits, and software, for preparing, reacting, detecting, and/or analyzing samples in droplet-based assay systems, among others. The disclosure emphasizes, but is not limited to, a disposable cartridge with lysis chamber and droplet chamber, particularly for use in droplet-based assays.

33 Claims, 9 Drawing Sheets

Related U.S. Application Data filed on Feb. 5, 2009, provisional application No. 61/271,538, filed on Jul. 21, 2009, provisional application No. 61/275,731, filed on Sep. 1, 2009, provisional application No. 61/277,200, filed on Sep. 21, 2009, provisional application No. 61/277,203, filed on Sep. 21, 2009, provisional application No. 61/277,204, filed on Sep. 21, 2009, provisional application No. 61/277,216, filed on Sep. 21, 2009, provisional application No. 61/277,249, filed on Sep. 21, 2009, provisional application No. 61/277,270, filed on Sep. 22, 2009.

(51) Int. Cl.
*B01F 3/08* (2006.01)
*B01F 13/00* (2006.01)
*B01L 3/02* (2006.01)
*B01L 3/00* (2006.01)
*G01N 21/3563* (2014.01)
*G01N 21/64* (2006.01)
*B01L 7/00* (2006.01)

(52) U.S. Cl.
CPC . *B01L 2200/0689* (2013.01); *B01L 2300/0816* (2013.01); *B01L 2300/0819* (2013.01); *B01L 2300/1822* (2013.01); *B01L 2400/0478* (2013.01); *B01L 2400/0487* (2013.01); *B01L 2400/0622* (2013.01); *G01N 2021/6439* (2013.01)

(56) References Cited

U.S. PATENT DOCUMENTS

| | | |
|---|---|---|
| 4,201,691 A | 5/1980 | Asher et al. |
| 4,283,262 A | 8/1981 | Cormier et al. |
| 4,348,111 A | 9/1982 | Goulas et al. |
| 4,636,075 A | 1/1987 | Knollenberg |
| 4,948,961 A | 8/1990 | Hillman et al. |
| 5,055,390 A | 10/1991 | Weaver et al. |
| 5,176,203 A | 1/1993 | Larzul |
| 5,225,332 A | 7/1993 | Weaver et al. |
| 5,270,183 A | 12/1993 | Corbett et al. |
| 5,314,809 A | 5/1994 | Erlich et al. |
| 5,344,930 A | 9/1994 | Riess et al. |
| 5,422,277 A | 6/1995 | Connelly et al. |
| 5,538,667 A | 7/1996 | Hill et al. |
| 5,555,191 A | 9/1996 | Hripcsak |
| 5,585,069 A | 12/1996 | Zanzucchi et al. |
| 5,587,128 A | 12/1996 | Wilding et al. |
| 5,602,756 A | 2/1997 | Atwood et al. |
| 5,720,923 A | 2/1998 | Haff et al. |
| 5,736,314 A | 4/1998 | Hayes et al. |
| 5,779,977 A | 7/1998 | Haff et al. |
| 5,827,480 A | 10/1998 | Haff et al. |
| 5,856,174 A | 1/1999 | Lipshutz et al. |
| 5,912,945 A | 6/1999 | Da Silva et al. |
| 5,928,907 A | 7/1999 | Woudenberg et al. |
| 5,945,334 A | 8/1999 | Besemer et al. |
| 5,972,716 A | 10/1999 | Ragusa et al. |
| 5,980,936 A | 11/1999 | Krafft et al. |
| 5,994,056 A | 11/1999 | Higuchi |
| 6,033,880 A | 3/2000 | Haff et al. |
| 6,042,709 A | 3/2000 | Parce et al. |
| 6,057,149 A | 5/2000 | Burns et al. |
| 6,126,899 A | 10/2000 | Woudenberg et al. |
| 6,130,098 A | 10/2000 | Handique et al. |
| 6,143,496 A | 11/2000 | Brown et al. |
| 6,146,103 A | 11/2000 | Lee et al. |
| 6,171,785 B1 | 1/2001 | Higuchi |
| 6,175,669 B1 | 1/2001 | Colston et al. |
| 6,176,609 B1 | 1/2001 | Cleveland et al. |
| 6,177,479 B1 | 1/2001 | Nakajima et al. |
| 6,210,879 B1 | 4/2001 | Meloni et al. |
| 6,258,569 B1 | 7/2001 | Livak et al. |
| 6,281,254 B1 | 8/2001 | Nakajima et al. |
| 6,303,343 B1 * | 10/2001 | Kopf-Sill ................ 435/91.1 |
| 6,357,907 B1 | 3/2002 | Cleveland et al. |
| 6,384,915 B1 | 5/2002 | Everett et al. |
| 6,391,559 B1 | 5/2002 | Brown et al. |
| 6,440,706 B1 | 8/2002 | Vogelstein et al. |
| 6,466,713 B2 | 10/2002 | Everett et al. |
| 6,488,895 B1 | 12/2002 | Kennedy |
| 6,489,103 B1 | 12/2002 | Griffiths et al. |
| 6,494,104 B2 | 12/2002 | Kawakita et al. |
| 6,509,085 B1 | 1/2003 | Kennedy |
| 6,521,427 B1 | 2/2003 | Evans |
| 6,524,456 B1 | 2/2003 | Ramsey et al. |
| 6,540,895 B1 | 4/2003 | Spence et al. |
| 6,551,841 B1 | 4/2003 | Wilding et al. |
| 6,558,916 B2 | 5/2003 | Veerapandian et al. |
| 6,575,188 B2 | 6/2003 | Parunak |
| 6,602,472 B1 | 8/2003 | Zimmermann et al. |
| 6,620,625 B2 | 9/2003 | Wolk et al. |
| 6,637,463 B1 | 10/2003 | Lei et al. |
| 6,638,749 B1 | 10/2003 | Beckman et al. |
| 6,660,367 B1 | 12/2003 | Yang et al. |
| 6,663,619 B2 | 12/2003 | Odrich et al. |
| 6,664,044 B1 | 12/2003 | Sato |
| 6,670,153 B2 | 12/2003 | Stern |
| 6,753,147 B2 | 6/2004 | Vogelstein et al. |
| 6,767,706 B2 | 7/2004 | Quake et al. |
| 6,773,566 B2 | 8/2004 | Shenderov |
| 6,808,882 B2 | 10/2004 | Griffiths et al. |
| 6,814,934 B1 | 11/2004 | Higuchi |
| 6,833,242 B2 | 12/2004 | Quake et al. |
| 6,900,021 B1 | 5/2005 | Harrison et al. |
| 6,905,885 B2 | 6/2005 | Colston et al. |
| 6,949,176 B2 | 9/2005 | Vacca et al. |
| 6,960,437 B2 | 11/2005 | Enzelberger et al. |
| 6,964,846 B1 | 11/2005 | Shuber |
| 7,010,391 B2 | 3/2006 | Handique et al. |
| 7,041,481 B2 | 5/2006 | Anderson et al. |
| 7,052,244 B2 | 5/2006 | Fouillet et al. |
| 7,081,336 B2 | 7/2006 | Bao et al. |
| 7,091,048 B2 | 8/2006 | Parce et al. |
| 7,094,379 B2 | 8/2006 | Fouillet et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,141,537 B2 | 11/2006 | Audenaert et al. |
| 7,192,557 B2 | 3/2007 | Wu et al. |
| 7,198,897 B2 | 4/2007 | Wangh et al. |
| 7,238,268 B2 | 7/2007 | Ramsey et al. |
| 7,244,567 B2 | 7/2007 | Chen et al. |
| 7,252,943 B2 | 8/2007 | Griffiths et al. |
| 7,268,167 B2 | 9/2007 | Higuchi et al. |
| 7,268,179 B2 | 9/2007 | Brown |
| 7,270,786 B2 | 9/2007 | Parunak et al. |
| 7,279,146 B2 | 10/2007 | Nassef et al. |
| 7,294,468 B2 | 11/2007 | Bell et al. |
| 7,294,503 B2 | 11/2007 | Quake et al. |
| 7,306,929 B2 | 12/2007 | Ignatov et al. |
| 7,312,085 B2 | 12/2007 | Chou et al. |
| 7,323,305 B2 | 1/2008 | Leamon et al. |
| 7,368,233 B2 | 5/2008 | Shuber et al. |
| 7,375,140 B2 | 5/2008 | Higuchi et al. |
| 7,423,751 B2 | 9/2008 | Hairston et al. |
| 7,429,467 B2 | 9/2008 | Holliger et al. |
| 7,567,596 B2 | 7/2009 | Dantus et al. |
| 7,579,172 B2 | 8/2009 | Cho et al. |
| 7,595,195 B2 | 9/2009 | Lee et al. |
| 7,622,280 B2 | 11/2009 | Holliger et al. |
| 7,629,123 B2 | 12/2009 | Millonig et al. |
| 7,776,927 B2 | 8/2010 | Chu et al. |
| 7,807,920 B2 | 10/2010 | Linke et al. |
| 7,842,457 B2 | 11/2010 | Berka et al. |
| 8,399,198 B2 | 3/2013 | Hiddessen et al. |
| 2001/0046701 A1 | 11/2001 | Schulte et al. |
| 2002/0021866 A1 | 2/2002 | Everett et al. |
| 2002/0022261 A1 | 2/2002 | Anderson et al. |
| 2002/0060156 A1 | 5/2002 | Mathies et al. |

(56) References Cited

U.S. PATENT DOCUMENTS

| | | |
|---|---|---|
| 2002/0068357 A1 | 6/2002 | Mathies et al. |
| 2002/0093655 A1 | 7/2002 | Everett et al. |
| 2002/0141903 A1 | 10/2002 | Parunak et al. |
| 2002/0142483 A1 | 10/2002 | Yao et al. |
| 2002/0151040 A1 | 10/2002 | O'Keefe et al. |
| 2002/0164820 A1 | 11/2002 | Brown |
| 2002/0195586 A1 | 12/2002 | Auslander et al. |
| 2003/0001121 A1 | 1/2003 | Hochstein |
| 2003/0003054 A1 | 1/2003 | McDonald et al. |
| 2003/0003441 A1 | 1/2003 | Colston et al. |
| 2003/0008308 A1 | 1/2003 | Enzelberger et al. |
| 2003/0027150 A1 | 2/2003 | Katz |
| 2003/0027244 A1 | 2/2003 | Colston et al. |
| 2003/0027352 A1 | 2/2003 | Hooper et al. |
| 2003/0032172 A1 | 2/2003 | Colston, Jr. et al. |
| 2003/0049659 A1 | 3/2003 | Lapidus et al. |
| 2003/0087300 A1 | 5/2003 | Knapp et al. |
| 2003/0170698 A1 | 9/2003 | Gascoyne et al. |
| 2003/0180765 A1 | 9/2003 | Traverso et al. |
| 2003/0204130 A1 | 10/2003 | Colston, Jr. et al. |
| 2004/0007463 A1 | 1/2004 | Ramsey et al. |
| 2004/0038385 A1 | 2/2004 | Langlois et al. |
| 2004/0067493 A1 | 4/2004 | Matsuzaki et al. |
| 2004/0068019 A1 | 4/2004 | Higuchi et al. |
| 2004/0074849 A1 | 4/2004 | Brown et al. |
| 2004/0171055 A1 | 9/2004 | Brown |
| 2004/0180346 A1 | 9/2004 | Anderson et al. |
| 2004/0208792 A1 | 10/2004 | Linton et al. |
| 2005/0036920 A1 | 2/2005 | Gilbert |
| 2005/0042639 A1 | 2/2005 | Knapp et al. |
| 2005/0064460 A1 | 3/2005 | Holliger et al. |
| 2005/0079510 A1 | 4/2005 | Berka et al. |
| 2005/0112541 A1 | 5/2005 | Durack et al. |
| 2005/0172476 A1 | 8/2005 | Stone et al. |
| 2005/0202429 A1 | 9/2005 | Trau et al. |
| 2005/0221279 A1 | 10/2005 | Carter et al. |
| 2005/0221373 A1 | 10/2005 | Enzelberger et al. |
| 2005/0227264 A1 | 10/2005 | Nobile et al. |
| 2005/0239192 A1 | 10/2005 | Nasarabadi et al. |
| 2005/0277125 A1 | 12/2005 | Benn et al. |
| 2005/0282206 A1 | 12/2005 | Corbett et al. |
| 2006/0014187 A1 | 1/2006 | Li et al. |
| 2006/0057599 A1 | 3/2006 | Dzenitis et al. |
| 2006/0077755 A1 | 4/2006 | Higuchi et al. |
| 2006/0079583 A1 | 4/2006 | Higuchi et al. |
| 2006/0079584 A1 | 4/2006 | Higuchi et al. |
| 2006/0079585 A1 | 4/2006 | Higuchi et al. |
| 2006/0094108 A1 | 5/2006 | Yoder et al. |
| 2006/0106208 A1* | 5/2006 | Nochumson et al. ........ 536/25.4 |
| 2006/0188463 A1 | 8/2006 | Kim et al. |
| 2007/0003442 A1 | 1/2007 | Link et al. |
| 2007/0010974 A1 | 1/2007 | Nicoli et al. |
| 2007/0048756 A1 | 3/2007 | Mei et al. |
| 2007/0109542 A1 | 5/2007 | Tracy et al. |
| 2007/0166200 A1 | 7/2007 | Zhou et al. |
| 2007/0195127 A1 | 8/2007 | Ahn et al. |
| 2007/0196397 A1 | 8/2007 | Torii et al. |
| 2007/0202525 A1 | 8/2007 | Quake et al. |
| 2007/0231393 A1 | 10/2007 | Ritter et al. |
| 2007/0242111 A1 | 10/2007 | Pamula et al. |
| 2007/0248956 A1 | 10/2007 | Buxbaum et al. |
| 2007/0258083 A1 | 11/2007 | Heppell et al. |
| 2007/0275415 A1 | 11/2007 | Srinivasan et al. |
| 2008/0003142 A1 | 1/2008 | Link et al. |
| 2008/0014589 A1 | 1/2008 | Link et al. |
| 2008/0038810 A1 | 2/2008 | Pollack et al. |
| 2008/0070862 A1 | 3/2008 | Laster et al. |
| 2008/0090244 A1 | 4/2008 | Knapp et al. |
| 2008/0138815 A1 | 6/2008 | Brown et al. |
| 2008/0145923 A1 | 6/2008 | Hahn et al. |
| 2008/0153091 A1 | 6/2008 | Brown et al. |
| 2008/0160525 A1 | 7/2008 | Brown et al. |
| 2008/0161420 A1 | 7/2008 | Shuber |
| 2008/0166793 A1 | 7/2008 | Beer et al. |
| 2008/0169184 A1 | 7/2008 | Brown et al. |
| 2008/0169195 A1 | 7/2008 | Jones et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171380 A1 | 7/2008 | Brown et al. |
| 2008/0171382 A1 | 7/2008 | Brown et al. |
| 2008/0213766 A1 | 9/2008 | Brown et al. |
| 2008/0214407 A1 | 9/2008 | Remacle et al. |
| 2008/0262384 A1 | 10/2008 | Wiederkehr et al. |
| 2008/0268436 A1 | 10/2008 | Duan et al. |
| 2008/0274455 A1 | 11/2008 | Puskas et al. |
| 2008/0280331 A1 | 11/2008 | Davies et al. |
| 2008/0280865 A1 | 11/2008 | Tobita |
| 2008/0280955 A1 | 11/2008 | McCamish |
| 2008/0314761 A1 | 12/2008 | Herminghaus et al. |
| 2009/0012187 A1 | 1/2009 | Chu et al. |
| 2009/0026082 A1 | 1/2009 | Rothberg et al. |
| 2009/0029867 A1 | 1/2009 | Reed et al. |
| 2009/0035770 A1 | 2/2009 | Mathies et al. |
| 2009/0035838 A1 | 2/2009 | Quake et al. |
| 2009/0061428 A1 | 3/2009 | McBride et al. |
| 2009/0068170 A1 | 3/2009 | Weitz et al. |
| 2009/0069194 A1 | 3/2009 | Ramakrishnan |
| 2009/0098044 A1 | 4/2009 | Kong et al. |
| 2009/0114043 A1 | 5/2009 | Cox |
| 2009/0131543 A1 | 5/2009 | Weitz et al. |
| 2009/0162929 A1 | 6/2009 | Ikeda |
| 2009/0176271 A1 | 7/2009 | Durack et al. |
| 2009/0203063 A1 | 8/2009 | Wheeler et al. |
| 2009/0217742 A1 | 9/2009 | Chiu et al. |
| 2009/0220434 A1 | 9/2009 | Sharma |
| 2009/0235990 A1 | 9/2009 | Beer |
| 2009/0239308 A1 | 9/2009 | Dube et al. |
| 2009/0291435 A1 | 11/2009 | Unger et al. |
| 2009/0311713 A1 | 12/2009 | Pollack et al. |
| 2009/0325184 A1 | 12/2009 | Woudenberg et al. |
| 2009/0325234 A1 | 12/2009 | Gregg et al. |
| 2009/0325236 A1 | 12/2009 | Griffiths et al. |
| 2010/0009360 A1 | 1/2010 | Costa et al. |
| 2010/0020565 A1 | 1/2010 | Seward |
| 2010/0022414 A1 | 1/2010 | Link et al. |
| 2010/0041046 A1 | 2/2010 | Chiu et al. |
| 2010/0047808 A1 | 2/2010 | Reed et al. |
| 2010/0069250 A1 | 3/2010 | White, III et al. |
| 2010/0069263 A1 | 3/2010 | Shendure et al. |
| 2010/0092973 A1 | 4/2010 | Davies et al. |
| 2010/0137163 A1 | 6/2010 | Link et al. |
| 2010/0173394 A1 | 7/2010 | Colston, Jr. et al. |
| 2010/0248385 A1 | 9/2010 | Tan et al. |
| 2010/0261229 A1 | 10/2010 | Lau et al. |
| 2010/0304446 A1 | 12/2010 | Davies et al. |
| 2010/0304978 A1 | 12/2010 | Deng et al. |
| 2011/0000560 A1 | 1/2011 | Miller et al. |
| 2011/0027394 A1 | 2/2011 | McClements et al. |
| 2011/0053798 A1 | 3/2011 | Hindson et al. |
| 2011/0070589 A1 | 3/2011 | Belgrader et al. |
| 2011/0086780 A1 | 4/2011 | Colston, Jr. et al. |
| 2011/0092373 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0118151 A1 | 5/2011 | Eshoo et al. |
| 2011/0160078 A1 | 6/2011 | Fodor et al. |
| 2011/0177563 A1 | 7/2011 | Hahn et al. |
| 2011/0183330 A1 | 7/2011 | Lo et al. |
| 2011/0212516 A1 | 9/2011 | Ness et al. |
| 2011/0217712 A1 | 9/2011 | Hiddessen et al. |
| 2011/0217736 A1 | 9/2011 | Hindson |
| 2011/0218123 A1 | 9/2011 | Weitz et al. |
| 2011/0244455 A1 | 10/2011 | Larson et al. |
| 2011/0250597 A1 | 10/2011 | Larson et al. |
| 2011/0311978 A1 | 12/2011 | Makarewicz, Jr. et al. |
| 2012/0021423 A1 | 1/2012 | Colston, Jr. et al. |
| 2012/0122714 A1 | 5/2012 | Samuels et al. |
| 2012/0152369 A1 | 6/2012 | Hiddessen et al. |
| 2012/0171683 A1 | 7/2012 | Ness et al. |
| 2012/0190032 A1 | 7/2012 | Ness et al. |
| 2012/0190033 A1 | 7/2012 | Ness et al. |
| 2012/0194805 A1 | 8/2012 | Ness et al. |

(56) References Cited

U.S. PATENT DOCUMENTS

| | | |
|---|---|---|
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0264646 A1 | 10/2012 | Link et al. |
| 2012/0302448 A1 | 11/2012 | Hutchison et al. |
| 2012/0309002 A1 | 12/2012 | Link |
| 2012/0329664 A1 | 12/2012 | Saxonov et al. |
| 2013/0017551 A1 | 1/2013 | Dube |
| 2013/0040841 A1 | 2/2013 | Saxonov et al. |
| 2013/0045875 A1 | 2/2013 | Saxonov et al. |
| 2013/0059754 A1 | 3/2013 | Tzonev |
| 2013/0064776 A1 | 3/2013 | El Harrak et al. |
| 2013/0084572 A1 | 4/2013 | Hindson et al. |
| 2013/0099018 A1 | 4/2013 | Miller et al. |
| 2013/0109575 A1 | 5/2013 | Kleinschmidt et al. |

FOREIGN PATENT DOCUMENTS

| | | |
|---|---|---|
| GB | 1 503 163 | 3/1978 |
| GB | 2 097 692 | 11/1982 |
| JP | 0295433 | 4/1990 |
| WO | 82/02562 | 8/1982 |
| WO | 84/02000 | 5/1984 |
| WO | 92/01812 | 2/1992 |
| WO | 94/05414 | 3/1994 |
| WO | 96/12194 | 4/1996 |
| WO | 98/00231 | 1/1998 |
| WO | 98/16313 | 4/1998 |
| WO | 98/44151 | 10/1998 |
| WO | 98/44152 | 10/1998 |
| WO | 98/47003 | 10/1998 |
| WO | 01/07159 | 2/2001 |
| WO | 01/12327 | 2/2001 |
| WO | 02/23163 | 3/2002 |
| WO | 02/060584 | 8/2002 |
| WO | 02/068104 | 9/2002 |
| WO | 02/081490 | 10/2002 |
| WO | 02/081729 | 10/2002 |
| WO | 03/016558 | 2/2003 |
| WO | 03/042410 | 5/2003 |
| WO | 03/072258 | 9/2003 |
| WO | 2004/040001 | 5/2004 |
| WO | 2005/007812 | 1/2005 |
| WO | 2005/010145 | 2/2005 |
| WO | 2005/021151 | 3/2005 |
| WO | 2005/023091 | 3/2005 |
| WO | 2005/055807 | 6/2005 |
| WO | 2005/073410 | 8/2005 |
| WO | 2005/075683 | 8/2005 |
| WO | 2006/023719 | 3/2006 |
| WO | 2006/027757 | 3/2006 |
| WO | 2006/038035 | 4/2006 |
| WO | 2006/086777 | 8/2006 |
| WO | 2006/095981 | 9/2006 |
| WO | 2007/091228 | 8/2007 |
| WO | 2007/091230 | 8/2007 |
| WO | 2007/092473 | 8/2007 |
| WO | 2007/133710 | 11/2007 |
| WO | 2008/021123 | 2/2008 |
| WO | 2008/024114 | 2/2008 |
| WO | 2008/063227 | 5/2008 |
| WO | 2008/070074 | 6/2008 |
| WO | 2008/070862 | 6/2008 |
| WO | 2008/109176 | 9/2008 |
| WO | 2008/109878 | 9/2008 |
| WO | 2008/112177 | 9/2008 |
| WO | 2009/002920 | 12/2008 |
| WO | 2009/015863 | 2/2009 |
| WO | 2009/049889 | 4/2009 |
| WO | 2009/085246 | 7/2009 |
| WO | 2010/001419 | 1/2010 |
| WO | 2010/018465 | 2/2010 |
| WO | 2011/034621 | 3/2011 |
| WO | 2011/079176 | 6/2011 |

OTHER PUBLICATIONS

Young, Lee W., Authorized officer, International Searching Authority, Written Opinion of the International Searching Authority, PCT Application Serial No. PCT/US2009/05317; mailing date: Nov. 20, 2009.

J. Smid-Korbar et al., "Efficiency and usability of silicone surfactants in emulsions," International Journal of Cosmetic Science 12, pp. 135-139, (1990), presented at the 15th IFSCC International Congress, Sep. 26-29, 1988, London.

A. Chittofrati et al., "Perfluoropolyether microemulsions," Progress in Colloid & Polymer Science 79, pp. 218-225, (1989).

Steven A. Snow, "Synthesis and Characterization of Zwitterionic Silicone Sulfobetaine Surfactants," Langmuir, vol. 6, No. 2, American Chemical Society, pp. 385-391, (1990).

Polydimethylsiloxane, 5 pgs., published in FNP 52 (1992).

Russell Higuchi et al., "Kinetic PCR Analysis: Real-time Monitoring of DNA Amplification Reactions," Bio/Technology vol. II, pp. 1026-1030, Sep. 11, 1993.

D. A. Newman et al., "Phase Behavior of Fluoroether-Functional Amphiphiles in Supercritical Carbon Dioxide," The Journal of Supercritical Fluids, vol. 6, No. 4, pp. 205-210, (1993).

Y. Sela et al., "Newly designed polysiloxane-graft-poly (oxyethylene) copolymeric surfactants: preparation, surface activity and emulsification properties," Colloid & Polymer Science 272, pp. 684-691, (1994).

M. Gasperlin et al., "The structure elucidation of semisolid w/o emulsion systems containing silicone surfactant," International Journal of Pharmaceutics 107, pp. 51-56, (1994).

Mieczyslaw A. Piatyszek et al., "Detection of telomerase activity in human cells and tumors by a telomeric repeat amplification protocol (TRAP)," Methods in Cell Science 17, pp. 1-15, (1995).

Anthony P. Shuber et al., "A Simplified Procedure for Developing Multiplex PCRs," Genome Research, published by Cold Spring Harbor Laboratory Press, pp. 488-493, (1995).

A. V. Yazdi et al., "Highly Carbon Dioxide Soluble Surfactants, Dispersants and Chelating Agents," Fluid Phase Equilibria, vol. 117, pp. 297-303, (1996).

Ariel A. Avilion et al., "Human Telomerase RNA and Telomerase Activity in Immortal Cell Lines and Tumor Tissues," Cancer Research 56, pp. 645-650, Feb. 1, 1996.

Shuming Nie et al., "Optical Detection of Single Molecules," Annu. Rev. Biophys. BiomoL Struct. vol. 26, pp. 567-596, (1997).

Edith J. Singley et al., "Phase behavior and emulsion formation of novel fluoroether amphiphiles in carbon dioxide," Fluid Phase Equilibria 128, pp. 199-219, (1997).

Olga Kalinina et al., "Nanoliter scale PCR with TaqMan Detection," Nucleic Acids Research, vol. 25, No. 10 pp. 1999-2004, (1997).

Zhen Guo et al , "Enhanced discrimination of single nucleotide polymorphisms by artificial mismatch hybridization," Nature Biotechnology vol. 15, pp. 331-335, Apr. 1997.

E. G. Ghenciu et al., "Affinity Extraction into Carbon Dioxide. 1. Extraction of Avidin Using a Biotin-Functional Fluoroether Surfactant," Ind. Eng. Chem. Res. vol. 36, No. 12, pp. 5366-5370, Dec. 1, 1997.

Paschalis Alexandridis, Structural Polymorphism of Poly(ethylene oxide)-Poly(propylene oxide) Block Copolymers in Nonaqueous Polar Solvents, Macromolecules, vol. 31, No. 20, pp. 6935-6942, Sep. 12, 1998.

Sandro R. P. Da Rocha et al., "Effect of Surfactants on the Interfacial Tension and Emulsion Formation between Water and Carbon Dioxide," Langmuir, vol. 15, No. 2, pp. 419-428, (1999), published on web Dec. 29, 1998.

Bert Vogelstein et al., "Digital PCR," Proc. Natl. Acad. Sci. USA, vol. 96, pp. 9236-9241, Aug. 1999.

Anthony J. O'Lenick, Jr., "Silicone Emulsions and Surfactants," Journal of Surfactants and Detergents, vol. 3, No. 3, Jul. 2000.

N. Garti et al., "Water Solubilization in Nonionic Microemulsions Stabilized by Grafted Siliconic Emulsifiers," Journal of Colloid and Interface Science vol. 233, pp. 286-294, (2001).

(56) References Cited

OTHER PUBLICATIONS

Shinji Katsura et al., "Indirect micromanipulation of single molecules in water-in-oil emulsion," Electrophoresis, vol. 22, pp. 289-293, (2001).

Hironobu Kunieda et al., "Effect of Hydrophilic- and Hydrophobic-Chain Lengths on the Phase Behavior of A-B-type Silicone Surfactants in Water," J. Phys. Chem. B, vol. 105, No. 23, pp. 5419-5426, (2001).

Hidenori Nagai et al., "Development of a Microchamber Array for Picoliter PCR," Analytical Chemistry, vol. 73, No. 5, pp. 1043-1047, Mar. 1, 2001.

Christopher B. Price, "Regular Review Point of Care Testing," BMJ, vol. 322, May 26, 2001.

3M Specialty Materials, "3M Fluorinert Electronic Liquid FC-3283," product information guide, issued Aug. 2001.

Ivonne Schneegaß et al., "Miniaturized flow-through PCR with different template types in a silicon chip thermocycler," Lab on a Chip, vol. 1, pp. 42-49, (2001).

Randla M. Hill, "Silicone surfactants—new developments," Current Opinion in Colloid & Interface Science 7, pp. 255-261, (2002).

Richard M. Cawthon, "Telomere measurement by quantitative PCR," Nucleic Acids Research, vol. 30, No. 10, pp. 1-6, (2002).

Anfeng Wang et al., "Direct Force Measurement of Silicone- and Hydrocarbon-Based ABA Triblock Surfactants in Alcoholic Media by Atomic Force Mircroscopy," Journal of Colloid and Interface Science 256, pp. 331-340 (2002).

Shelley L. Anna et al., "Formation of dispersions using "flow focusing" in microchannels," Applied Physics Letters, vol. 82, No. 3, Jan. 20, 2003.

Goldschmidt GMBH, "Abil® EM 90 Emulsifier for the formulation of cosmetic W/O creams and lotions," degussa. creating essentials brochure, pp. 1-7, May 2003.

Purnendu K. Dasgupta et al., "Light emitting diode-based detectors Absorbance, fluorescence and spectroelectrochemical measurements in a planar flow-through cell," Analytica Chimica Acta 500, pp. 337-364, (2003).

R. G. Rutledge et al., "Mathematics of quantitative kinetic PCR and the application of standard curves," Nucleic Acids Research, vol. 31, No. 16, pp. 1-6, (2003).

Chunming Ding et al., "Direct molecular haplotyping of long-range genomic DNA with M1-PCR," PNAS, vol. 100, No. 13, pp. 7449-7453, Jun. 24, 2003.

Devin Dressman et al., "Transforming single DNA molecules into fluorescent magnetic particles for detection and enumeration of genetic variations," PNAS, vol. 100, No. 15, Jul. 22, 2003.

Ulf Landegren et al., "Padlock and proximity probes for in situ and array-based analyses: tools for the post-genomic era," Comp. Funct. Genom, vol. 4, pp. 525-530, (2003).

Gudrun Pohl et al., "Principle and applications of digital PCR" review, www.future-drugs.com, Expert Rev. Mol. Diagn. 4(1), pp. 41-47, (2004).

Groff M. Schroeder et al., "Introduction to Flow Cytometry" version 5.1, 182 pgs. (2004).

Stéphane Swillens et al., "Instant evaluation of the absolute initial number of cDNA copies from a single real-time PCR curve," Nucleic Acids Research, vol. 32, No. 6, pp. 1-6, (2004).

Mats Gullberg et al., "Cytokine detection by antibody-based proximity ligation," PNAS, vol. 101, No. 22, pp. 8420-8424, Jun. 1, 2004.

Tianhao Zhang et al., "Behavioral Modeling and Performance Evaluation of Microelectrofluidics-Based PCR Systems Using SystemC," IEEE Transactions on Computer-Aided Design of Integrated Circuits and Systems, vol. 23, No. 6, pp. 843-858, Jun. 2004.

R. G. Rutledge, "Sigmoidal curve-fitting redefines quantitative real-time PCR with the prospective of developing automated high-throughput applications," Nucleic Acids Research. vol. 32, No. 22, pp. 1-8, (2004).

L. Spencer Roach et al., "Controlling Nonspecific Protein Absorption in a Plug-Based Microfluidic System by Controlling Interfacial Chemistry Using Fluorous-Phase Surfactants," Analytical Chemistry vol. 77, No. 3, pp. 785-796, Feb. 1, 2005.

Kevin D. Dorfman et al., "Contamination-Free Continuous Flow Microfluidic Polymerase Chain Reaction for Quantitative and Clinical Applications," Analytical Chemistry vol. 77, No. 11, pp. 3700-3704, Jun. 1, 2005.

James G. Wetmur et al., "Molecular haplotyping by linking emulsion PCR: analysis of paraoxonase 1 haplotypes and phenotypes," Nucleic Acids Research, vol. 33, No. 8, pp. 2615-2619, (2005).

Piotr Garstecki et al., "Mechanism for Flow-Rate Controlled Breakup in Confined Geometries: A Route to Monodisperse Emulsions," Physical Review Letters, 164501, pp. 164501-1-164501-4, Apr. 29, 2005.

Anna Musyanovych et al., "Miniemulsion Droplets as Single Molecule Nanoreactors for Polymerase Chain Reaction," Biomacromolecules, vol. 6, No. 4, pp. 1824-1828, (2005).

Max Chabert et al., "Droplet fusion by alternating current (AC) field electrocoalescence in microchannels," Electrophoresis, vol. 26, pp. 3706-3715, (2005).

Takaaki Kojima et al., "PCR amplification from single DNA molecules on magnetic beads in emulsion: application for high-throughput screening of transcription factor targets," Nucleic Acids Research, vol. 33, No. 17, pp. 1-9, (2005).

Marcel Margulies et al., "Genome sequencing in microfabricated high-density picolitre reactors," Nature, vol. 437, 51 pgs., Sep. 15, 2005.

Kristofer J. Thurecht et al., "Investigation of spontaneous microemulsion formation in supercritical carbon dioxide using high-pressure NMR," Journal of Supercritical Fluids, vol. 38, pp. 111-118, (2006).

Toshko Zhelev et al., "Heat Integration in Micro-Fluidic Devices," 16$^{th}$ European Symposium on Computer Aided Process Engineering and 9$^{th}$ International Symposium on Process Systems Engineering, pp. 1863-1868 published by Elsevier B.V. (2006).

Piotr Garstecki et al., "Formation of droplets and bubbles in a microfluidic T-junction—scaling and mechanism of break-up," Lab on a Chip, vol. 6, pp. 437-446, (2006).

Darren R. Link et al., "Electric Control of Droplets in Microfluidic Devices," Angewandte Chemie Int. Ed., vol. 45, pp. 2556-2560, (2006).

Peter Fielden et al., "Micro-Droplet Technology for High Throughout Systems and Methods," 1 pg., Mar. 8, 2006.

David Emerson et al., "Microfluidic Modelling Activities at C3M," Centre for Microfluidics & Microsystems Modelling, Daresbury Laboratory, pp. 1-26, May 15, 2006.

Richard Williams et al., "Amplification of complex gene libraries by emulsion PCR," Nature Methods, vol. 3, No. 7, pp. 545-550, Jul. 2006.

John H. Leamon et al., "Overview: methods and applications for droplet compartmentalization of biology," Nature Methods, vol. 3, No. 7, pp. 541-543, Jul. 2006.

Andrew D. Griffiths et al., "Miniaturising the laboratory in emulsion droplets," Trends in Biotechnology, vol. 24, No. 9, pp. 395-402, Jul. 14, 2006.

Jian-Bing Fan et al., "Highly parallel genomic assays," Nature Reviews/Genetics, vol. 7, pp. 632-644, Aug. 2006.

Jonas Jarvius et al., "Digital quantification using amplified single-molecule detection," Nature Methods, vol. 3, No. 9, pp. 15 pgs, Sep. 2006.

Kan Liu et al., "Droplet-based synthetic method using microflow focusing and droplet fusion," Microfluid Nanfluid, vol. 3, pp. 239-243, (2007), published online Sep. 22, 2006.

Dimitris Glotsos et al., "Robust Estimation of Bioaffinity Assay Fluorescence Signals," IEEE Transactions on Information Technology in Biomedicine, vol. 10, No. 4, pp. 733-739, Oct. 2006.

Kristofer J. Thurecht et al., "Kinetics of Enzymatic Ring-Opening Polymerization of ε-Caprolactone in Supercritical Carbon Dioxide," Macromolecules, vol. 39, pp. 7967-7972, (2006).

Machiko Hori et al., "Uniform amplification of multiple DNAs by emulsion PCR," Biochemical and Biophysical Research Communications, vol. 352, pp. 323-328, (2007).

Frank Diehl et al., "Digital quantification of mutant DNA in cancer patients," Current Opinion in Oncology, vol. 19, pp. 36-42, (2007).

Delai L. Chen et al., "Using Three-Phase Flow of Immiscible Liquids to Prevent Coalescence of Droplets in Microfluidic Channels: Crite-

(56) References Cited

OTHER PUBLICATIONS ria to Identify the Third Liquid and Validation with Protein Crystallization," Langmuir, vol. 23, No. 4, pp. 2255-2260, (2007).
S. Mohr et al., "Numerical and experimental study of a droplet-based PCR chip," Microfluid Nanofluid, vol. 3, pp. 611-621, (2007).
Sigrun M. Gustafsdottir et al., "In vitro analysis of DNA-protein interactions by proximity ligation," PNAS, vol. 104, No. 9, pp. 3067-3072, Feb. 27, 2007.
Daniel J. Diekema et al., "Look before You Leap: Active Surveillance for Multidrug-Resistant Organisms," Healthcare Epidemiology • CID 2007:44, pp. 1101-1107 (Apr. 15), electronically published Mar. 2, 2007.
Charles N. Baroud et al., "Thermocapillary valve for droplet production and sorting," Physical Review E 75, 046302, pp. 046302-1-046302-5, Apr. 5, 2007.
Qinyu Ge et al., "Emulsion PCR-based method to detect Y chromosome microdeletions," Analytical Biochemistry, vol. 367, pp. 173-178, May 10, 2007.
Chunsun Zhang et al., "Miniaturized PCR chips for nucleic acid amplification and analysis: latest advances and future trends," Nucleic Acids Research, vol. 35, No. 13, pp. 4223-4237, Jun. 18, 2007.
Y. M. Dennis Lo et al., "Digital PCR for the molecular detection of fetal chromosomal aneuploidy," PNAS, vol. 104, No. 32, pp. 13116-13121, Aug. 7, 2007.
Dayong Jin et al., "Practical Time-Gated Luminescence Flow Cytometry. II: Experimental Evaluation Using UV LED Excitation," Cytometry Part A • 71A, pp. 797-808, Aug. 24, 2007.
Helen R. Hobbs et al., "Homogeneous Biocatalysis in both Fluorous Biphasic and Supercritical Carbon Dioxide Systems," Angewandte Chemie, vol. 119, pp. 8006-8009, Sep. 6, 2007.
Nathan Blow, "PCR's next frontier," Nature Methods, vol. 4, No. 10, pp. 869-875, Oct. 2007.
Nicole Pamme, "continuous flow separations in microfluidic devices," Lab on a Chip, vol. 7, pp. 1644-1659, Nov. 2, 2007.
N. Reginald Beer et al., "On-Chip, Real-Time, Single-Coy Polymerase Chain Reaction in Picoliter Droplets," Analytical Chemistry, vol. 79, No. 22, pp. 8471-8475, Nov. 15, 2007.
Yuejun Zhao et al., "Microparticle Concentration and Separation by Traveling-Wave Dielectrophoresis (twDEP) for Digital Microfluidics," Journal of Microelectromechanical Systems, vol. 16, No. 6, pp. 1472-1481, Dec. 2007.
SIGMA-Aldrich, "Synthesis of Mesoporous Materials," Material Matters, 3.1, 17, (2008).
Nick J. Carroll et al., "Droplet-Based Microfluidics for Emulsion and Solvent Evaporation Synthesis of Monodisperse Mesoporous Silica Microspheres," Langmuir, vol. 24, No. 3, pp. 658-661, Jan. 3, 2008.
Shia-Yen Teh et al., "Droplet microfluidics," Lab on a Chip, vol. 8, pp. 198-220, Jan. 11, 2008.
Chloroform (Phenomenex), Solvent Miscibility Table, Internet Archive WayBackMachine, 3 pgs., Feb. 1, 2008.
N. Reginald Beer et al., "On-Chip Single-Copy Real-Time Reverse-Transcription PCR in Isolated Picoliter Droplets," Analytical Chemistry, vol. 80, No. 6, pp. 1854-1858, Mar. 15, 2008.
Palani Kumaresan et al., "High-Throughput Single Copy DNA Amplification and Cell Analysis in Engineered Nanoliter Droplets," Analytical Chemistry, 17 pgs., Apr. 15, 2008.
Somil C. Mehta et a., "Mechanism of Stabilization of Silicone Oil—Water Emulsions Using Hybrid Siloxane Polymers," Langmuir, vol. 24, No. 9, pp. 4558-4563, Mar. 26, 2008.
Rhutesh K. Shah et al., "Polymers fit for function Making emulsions drop by drop," Materials Today, vol. 11, No. 4, pp. 18-27, Apr. 2008.
Mohamed Abdelgawad et al., "All-terrain droplet actuation," Lab on a Chip, vol. 8, pp. 672-677, Apr. 2, 2008.
Lung-Hsin Hung et al., "Rapid microfabrication of solvent-resistant biocompatible microfluidic devices," Lab on a Chip, vol. 8, pp. 983-987, Apr. 8, 2008.
Jenifer Clausell-Tormos et al., "Droplet-Based Microfluidic Platforms for the Encapsulation and Screening of Mammalian Cells and Multicellular Organisms," Chemistry & Biology, vol. 15, pp. 427-437, May 2008.
Vivienne N. Luk et al., "Pluronic Additives: A Solution to Sticky Problems in Digital Microfluidics," Langmuir, vol. 24, No. 12, pp. 6382-6289, May 16, 2008.
Yen-Heng Lin et al., "Droplet Formation Utilizing Controllable Moving-Wall Structures for Double-Emulsion Applications," Journal of Microelectromechanical Systems, vol. 17, No. 3, pp. 573-581, Jun. 2008.
Simant Dube et al., "Mathematical Analysis of Copy Number Variation in a DNA Sample Using Digital PCR on a Nanofluidic Device," PLoS One, vol. 3, Issue 8, pp. 1-9, Aug. 6, 2008.
Jian Qin et al., "Studying copy number variations using a nanofluidic platform," Nucleic Acids Research, vol. 36, No. 18, pp. 1-8, Aug. 18, 2008.
C. Holtze et al., "Biocompatible surfactants for water-in-fluorocarbon emulsions," Lab on a Chip, vol. 8, pp. 1632-1639, Sep. 2, 2008.
Margaret Macris Kiss et al., "High-Throughput Quantitative Polymerase Chain Reaction in Picoliter Droplets," Analytical Chemistry, 8 pgs., downloaded Nov. 17, 2008.
Jay Shendure et al., "Next-generation DNA sequencing," Nature Biotechnology, vol. 26, No. 10, pp. 1135-1145, Oct. 2008.
Bernhard G. Zimmermann et al., "Digital PCR: a powerful new tool for noninvasive prenatal diagnosis?," Prenatal Diagnosis, vol. 28 pp. 1087-1093, Nov. 10, 2008.
Avishay Bransky et al., "A microfluidic droplet generator based on a piezoelectric actuator," Lab on a Chip, vol. 9, pp. 516-520, Nov. 20, 2008.
David A. Weitz, "Novel Surfactants for Stabilizing Emulsions of Water or Hydrocarbon Oil-Based Droplets in a Fluorocarbon Oil Continuous Phase," Harvard Office of Technology Development: Available Technologies, pp. 1-3, downloaded Nov. 28, 2008.
Neil Reginald Beer et al., "Monodisperse droplet generation and rapid trapping for single molecule detection and reaction kinetics measurement," Lab on a Chip, vol. 9, pp. 841-844, Dec. 5, 2008.
Richard M. Cawthon, "Telomere length measurement by a novel monochrome multiplex quantitative PCR method," Nucleic Acids Research, vol. 37, No. 3, pp. 1-7, (2009).
Anthony J. O'Lenick, Jr., "Silicone Emulsions and Surfactants—A Review," Silicone Spectator, Silitech LLC, May, 2009 (original published May 2000).
Adam R. Abate et al., "Functionalized glass coating for PDMS microfluidic devices," Lab on a Chip Technology: Fabrication and Microfluidics, 11 pgs., (2009).
Chia-Hung Chen et al., "Janus Particles Templated from Double Emulsion Droplets Generated Using Microfluidics," Langmuir, vol. 29, No. 8, pp. 4320-4323, Mar. 18, 2009.
Luis M. Fidalgo et al., "Coupling Microdroplet Microreactors with Mass Spectrometry: Reading the Contents of Single Droplets Online," Angewandte Chemie, vol. 48, pp. 3665-3668, Apr. 7, 2009.
L1NAS Mazutis et al., "A fast and efficient microfluidic system for highly selective one-to-one droplet fusion," Lab on a Chip, vol. 9, pp. 2665-2672, Jun. 12, 2009.
Linas Mazutis et al., "Droplet-Based Microfluidic Systems for High-Throughput Single DNA Molecule Isothermal Amplification and Analysis," Analytical Chemistry, vol. 81, No. 12, pp. 4813-4821, Jun. 15, 2009.
Frank McCaughan et al., "Single-molecule genomics," Journal of Pathology, vol. 220, pp. 297-306, Nov. 19, 2009.
Suzanne Weaver et al., "Taking qPCR to a higher level: Analysis of Cnv reveals the power of high throughput qPCR to enhance quantitative resolution," Methods, vol. 50, pp. 271-276, Jan. 15, 2010.
Amelia L. Markey et al., "High-throughput droplet PCR," Methods, vol. 50, pp. 277-281, Feb. 2, 2010.
Yoon Sung Nam et al., "Nanosized Emulsions Stabilized by Semi-solid Polymer Interphase," Langmuir, ACS Publications, Jul. 23, 2010.
Tatjana Schütze et al., "A streamlined protocol for emulsion polymerase chain reaction and subsequent purification," Analytical Biochemistry, vol. 410, pp. 155-157, Nov. 25, 2010.

(56) References Cited

OTHER PUBLICATIONS

Somanath Bhat et al., "Effect of sustained elevated temperature prior to amplification on template copy number estimation using digital polymerase chain reaction," Analyst, vol. 136, pp. 724-732, (2011).

James G. Wetmur, et al., "Linking Emulsion PCR Haplotype Analysis," PCR Protocols, Methods in Molecular Biology, vol. 687, pp. 165-175, (2011).

Paul Vulto et al., "Phaseguides: a paradigm shift in microfluidic priming and emptying," Lab on a Chip, vol. 11, No. 9, pp. 1561-1700, May 7, 2011.

Thinxxs Microtechnology AG, "Emerald Biosystems: Protein Crystallization," 1 pg., downloaded Mar. 8, 2011.

Qun Zhong et al., "Multiplex digital PCR: breaking the one target per color barrier of quantitative PCR," Lab on a Chip, vol. 11, pp. 2167-2174, (2011).

Jiaqi Huang et al., "Rapid Screening of Complex DNA Samples by Single-Molecule Amplification and Sequencing," PLoS One, vol. 6, Issue 5, pp. 1-4, May 2011.

Burcu Kekevi et al., Synthesis and Characterization of Silicone-Based Surfactants as Anti-Foaming Agents, J. Surfact Deterg (2012), vol. 15, pp. 73-81, published online Jul. 7, 2011.

Leonardo B. Pinheiro et al., "Evaluation of a Droplet Digital Polymerase Chain Reaction Format for DNA Copy Number Quantification," Analytical Chemistry, vol. 84, pp. 1003-1011, Nov. 28, 2011.

Nicole L. Solimini et al., "Recurrent Hemizygous Deletions in Cancers May Optimize Proliferative Potential," Science, vol. 337, pp. 104-109, Jul. 6, 2012.

Labsmith, "Microfluid Components" webpage, downloaded Jul. 11, 2012.

Labsmith, "CapTite™ Microfluidic Interconnects" webpage, downloaded Jul. 11, 2012.

Nathan A. Tanner et al., "Simultaneous multiple target detection in real-time loop-mediated isothermal amplification," BioTechniques, vol. 53, pp. 8-19, Aug. 2012.

A. Scherer, California Institute of Technology, "Polymerase Chain Reactors" PowerPoint presentation, 24 pgs., date unknown.

Eschenback Optik GMBH, Optics for Concentrated Photovoltaics (CPV), 1 pg., date unknown.

\* cited by examiner

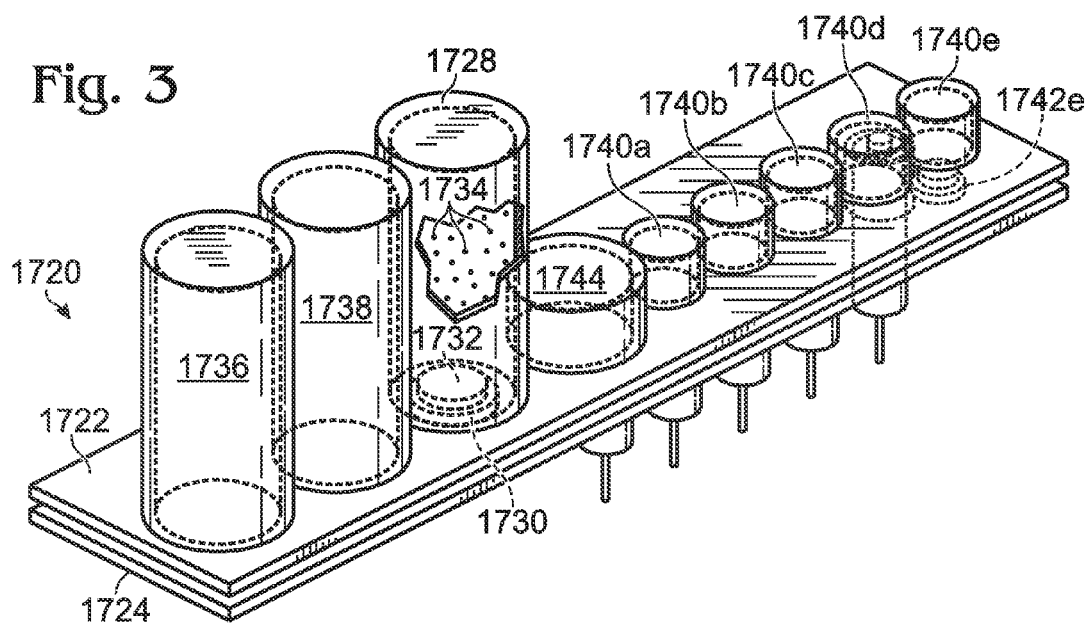
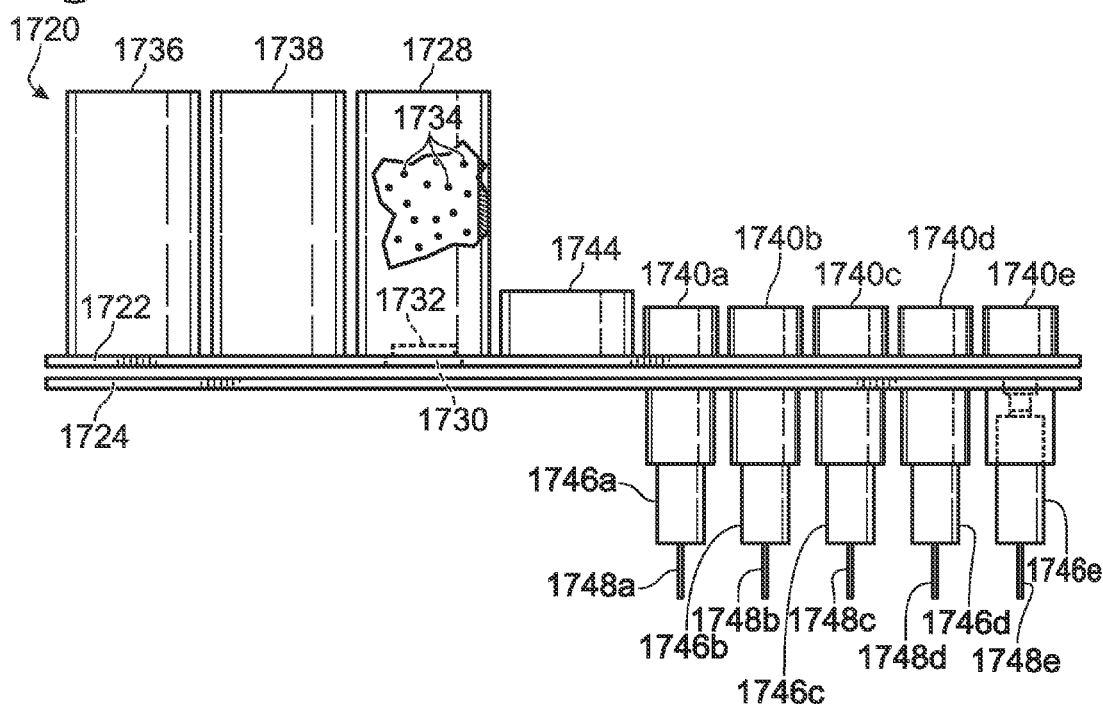

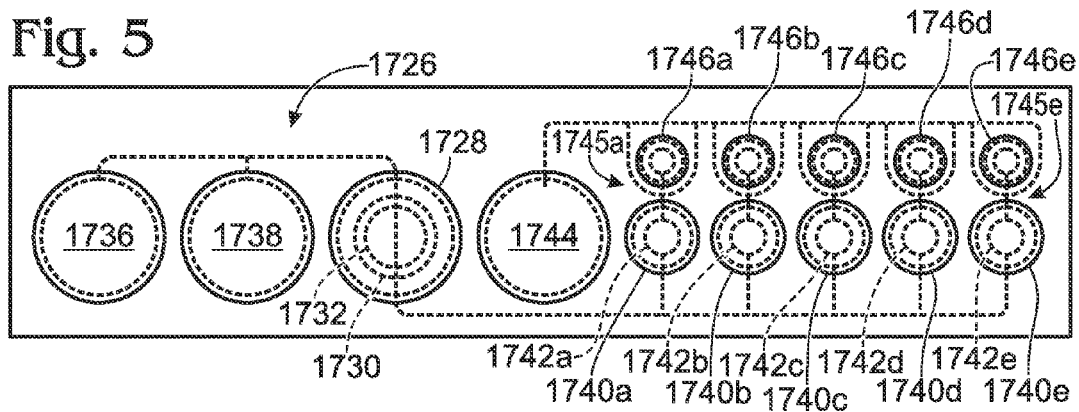
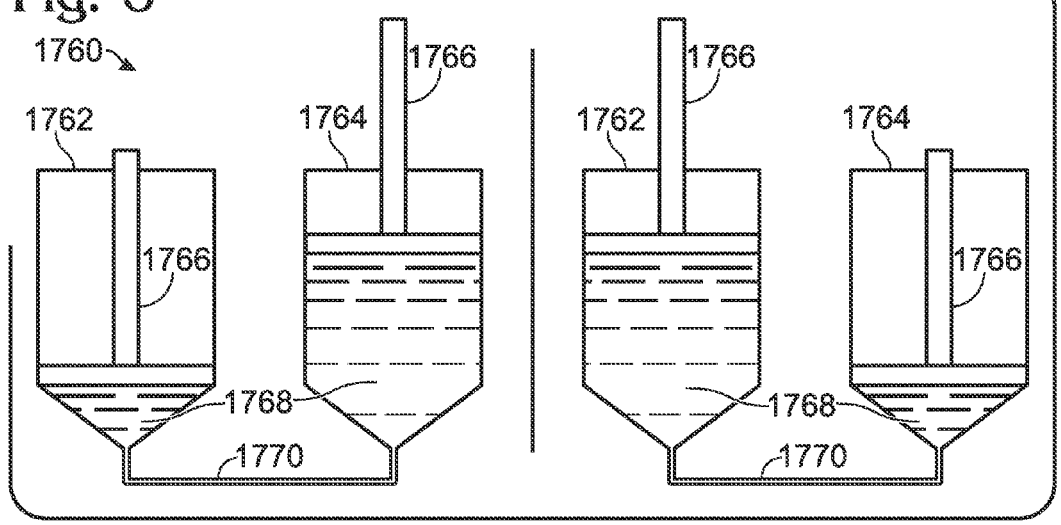

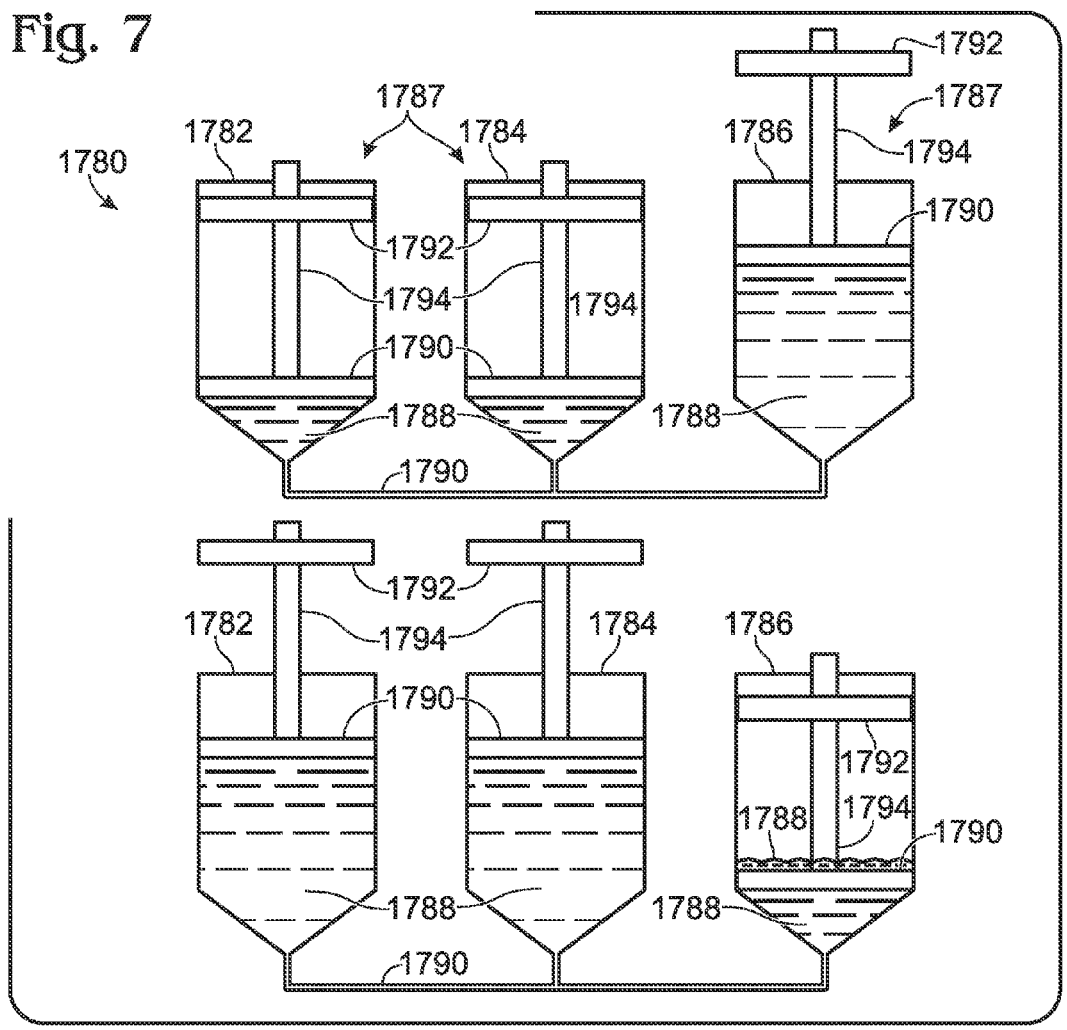
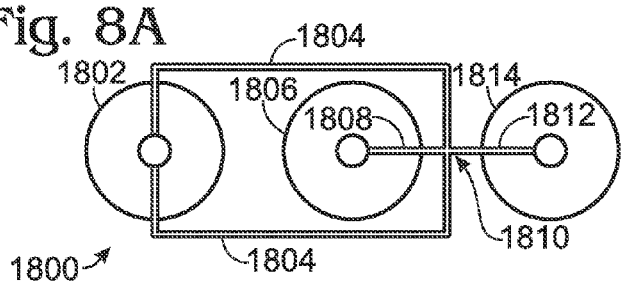
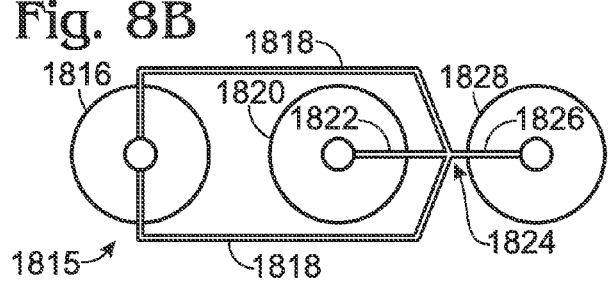

CARTRIDGE WITH LYSIS CHAMBER AND DROPLET GENERATOR

CROSS-REFERENCES TO PRIORITY APPLICATIONS

This application is a continuation of U.S. patent application Ser. No. 12/586,626, now U.S. Pat. No. 9,156,010, filed Sep. 23, 2009.

U.S. patent application Ser. No. 12/586,626, now U.S. Pat. No. 9,156,010, in turn, is based upon and claims the benefit under 35 U.S.C. §119(e) of the following U.S. provisional patent applications: Ser. No. 61/194,043, filed Sep. 23, 2008; Ser. No. 61/206,975, filed Feb. 5, 2009; Ser. No. 61/271,538, filed Jul. 21, 2009; Ser. No. 61/275,731, filed Sep. 1, 2009; Ser. No. 61/277,200, filed Sep. 21, 2009; Ser. No. 61/277,203, filed Sep. 21, 2009; Ser. No. 61/277,204, filed Sep. 21, 2009; Ser. No. 61/277,216, filed Sep. 21, 2009; Ser. No. 61/277,249, filed Sep. 21, 2009; and Ser. No. 61/277,270, filed Sep. 22, 2009.

Each of these patent applications is incorporated herein by reference in its entirety for all purposes.

CROSS-REFERENCES TO OTHER MATERIALS

This application incorporates by reference in their entireties for all purposes the following materials: U.S. Pat. No. 7,041,481, issued May 9, 2006; and Joseph R. Lakowicz, PRINCIPLES OF FLUORESCENCE SPECTROSCOPY ($2^{nd}$ Ed. 1999).

INTRODUCTION

Assays may be used to detect the presence and characteristics of certain nucleic acids in a sample. Nucleic acids are molecules found inside cells, organelles, and viruses. Nucleic acids, such as deoxyribonucleic acid (DNA) and ribonucleic acid (RNA), contain the unique blueprint, or genes, of each biological entity. Drug discovery, genetic analysis, pharmacogenomics, clinical diagnostics, and general biomedical research all use assays for nucleic acids. The most widely used assay for DNA analysis involves first amplifying a target DNA and then detecting the amplified target DNA with the use of a fluorescent dye. The most common amplification technique used today is the polymerase chain reaction (PCR).

PCR, which was developed in 1983, enables a single strand of nucleic acid to be amplified over a million times using alternating cycles of heating and cooling and fairly robust enzyme chemistry. The completion of the Human Genome Project, a 13-year effort by the U.S. Department of Energy and the National Institutes of Health to identify all of the approximately 20,000-25,000 genes in human DNA and to determine the sequence of the three billion chemical base pairs that make up human DNA, as well as the exponentially decreasing cost of sequencing, currently is spawning many new applications for this technology.

Real-time PCR (rtPCR) is a variant of PCR that involves monitoring a sample while DNA amplification is occurring. The benefit of this real-time capability is that it enables a practitioner to determine the amount of a target sequence of interest that was present initially in the sample before the amplification by PCR. The basic objective of rtPCR is to distinguish and measure precisely the amount of one or more specific nucleic acid target sequences in a sample, even if there is only a very small number of corresponding target molecules. rtPCR amplifies a specific target sequence in a sample and then monitors the amplification progress using fluorescence technology. During amplification, the speed with which the fluorescence signal reaches a threshold level correlates with the amount of original target sequence, thereby enabling quantification. However, the accuracy of this measurement is limited, because it relies on determining the point at which the fluorescence signal becomes exponential. Because most samples are complex (containing many different DNAs), because amplification efficiency can be extremely variable, and because a single cycle represents a doubling of the amount of nucleic acid target, typical measurement values can vary by as much as two- to four-fold or more. Moreover, reaction times for current rtPCR instruments are fundamentally limited by the need for thermal cycling of relatively large sample volumes and the thermal mass of reaction vessels.

Thus, there is a need for new systems of preparing, reacting, detecting, and analyzing samples.

SUMMARY

The present disclosure provides systems, including apparatus, methods, compositions, kits, and software, for preparing, reacting, detecting, and/or analyzing samples in droplet-based assays, among others. The disclosure emphasizes, but is not limited to, a disposable cartridge with lysis chamber and droplet chamber, particularly for use in droplet-based assays.

BRIEF DESCRIPTION OF THE DRAWINGS

FIGS. 3-5 are isometric, side elevation, and top views, respectively, of an interior portion of an exemplary disposable cartridge, suitable for performing some or all of the sample preparation steps in FIG. 1.

FIG. 6 is a schematic view of a two-chamber hydraulic mechanism, suitable for controlling fluid motion between the various chambers of a disposable cartridge, in accordance with aspects of the present disclosure.

FIG. 7 is a schematic view of a three-chamber hydraulic mechanism, which is similar to two-chamber mechanism of FIG. 6, suitable for controlling fluid motion between the various chambers of a disposable cartridge, in accordance with aspects of the present disclosure.

FIGS. 8A-8F are top views of various exemplary droplet generators, in accordance with aspects of the present disclosure.

DETAILED DESCRIPTION

Figure 1:
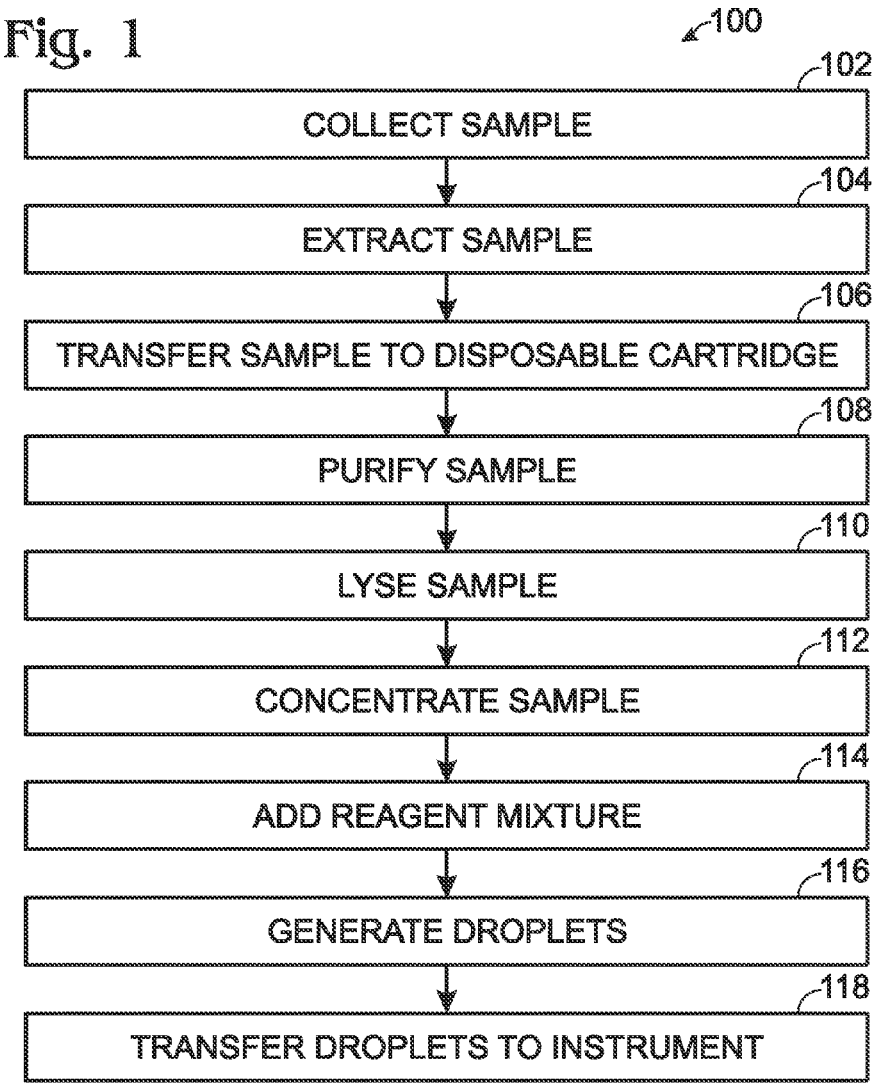
FIG. 1 is a flowchart depicting the steps of a DNA amplification method that may be performed within or in conjunction with a disposable cartridge of a DNA amplification system, in accordance with aspects of the present disclosure.

The present disclosure provides systems, including apparatus, methods, compositions, kits, and software, for preparing, reacting, detecting, and/or analyzing samples in droplet-based assays, among others. These systems may involve separating samples, such as clinical or environmental samples, into many small droplets, each containing about one copy of a nucleic acid target (DNA or RNA) or other analyte of interest. The nucleic acid or other analyte in these droplets may be reacted, detected, and/or analyzed, using any suitable technique(s). The preparation, reaction, detection, and/or analysis may be performed in series and/or in parallel, alone, or in combination with other processes. The disclosure emphasizes, but is not limited to, a disposable cartridge with lysis chamber and droplet chamber, particularly for use in droplet-based assays.

Samples, as used herein, may include any compound, composition, and/or mixture of interest, from any suitable source(s). A sample is the general subject of interest for a test that analyzes an aspect of the sample, such as an aspect related to at least one analyte that may be present in the sample. Samples may be analyzed in their natural state, as collected, and/or in an altered state, for example, following storage, preservation, extraction, lysis, dilution, concentration, purification, filtration, mixing with one or more reagents, pre-amplification, partitioning, or any combination thereof, among others. Clinical samples may include blood, saliva, urine, stool, sputum, mucous, milk, a fluid aspirate, a swab, and/or tissue, among others. Environmental samples may include water, soil, and/or air, among others. Research samples may include cultured cells, primary cells, viruses, small organisms, any of the clinical samples listed above, or the like. Additional samples may include foodstuffs, weapons components, suspected contaminants, and so on.

Preparing samples, and generating droplets, as used herein, may include, among others, (1) collecting a sample, such as a clinical, research, or environmental sample, (2) partitioning the sample, or a portion thereof, into droplets, and (3) treating the sample or droplets, if appropriate, to render them, or components thereof, capable of reaction. The preparation may be performed so that there is an average of less than one copy of interest, such as a target DNA or RNA molecule, per droplet. The droplets additionally may contain other moieties that are not of interest, including nontarget DNA or RNA In some cases, samples may be prepared using a discrete preparation cartridge/module, which may be disposable. The cartridge may perform, facilitate, and/or provide a site for any suitable combination of processes in sample preparation, including collection, extraction, lysis, purification, concentration, contact with one or more PCR reagents, and/or droplet generation, among others. Accordingly, the cartridge may contain one or more amplification reagents (e.g., one or more primers, probes, buffers, enzymes, or any combination thereof, among others). In addition, the cartridge may define at least one orifice from which droplets are formed. Furthermore, the cartridge may be connectable to any of the amplification/detection instruments disclosed herein or in the references listed above in the Cross-References, which are incorporated herein by reference. In some embodiments, an amplification instrument may control operation of the cartridge, such as control of valve switching in the cartridge and/or pumping of fluid into, within, through, and/or out of the cartridge, among others.

Reacting, as used herein, may include a chemical reaction, a binding interaction, a phenotypic change, or a combination thereof, which generally provides a detectable signal indicating occurrence and/or an extent of occurrence of a reaction. An exemplary reaction is an enzyme reaction that involves an enzyme-catalyzed conversion of a substrate to a product. The droplet-based assays disclosed herein may be used to perform any suitable enzyme reactions. For example, the reactions may be catalyzed by a kinase, nuclease, nucleotide cyclase, nucleotide ligase, nucleotide phosphodiesterase, polymerase, prenyl transferase, reporter enzyme (e.g., beta-galactosidase, chloramphenicol acetyl transferse, glucuronidase, or luciferase, among others), topoisomerase, etc. Reacting may include amplifying a nucleic acid, for example, using the polymerase chain reaction (PCR) or other suitable technique.

Detecting and analyzing, as used herein, may include observing and/or measuring, qualitatively and/or quantitatively, a condition of a sample (e.g., identity, amount, concentration, activity, potency, source, variation) using any suitable method(s) (e.g., optical (photoluminescence (e.g., fluorescence or phosphorescence), chemiluminescence, imaging, absorption, scattering) or nonoptical). Exemplary fluorescence techniques may include fluorescence intensity, fluorescence polarization (or anisotropy), fluorescence correlation spectroscopy, fluorescence photobleaching recovery, total internal reflection fluorescence, fluorescence energy transfer, fluorescence lifetime, and/or fluorescence imaging, among others. Analysis may be performed on individual droplets or groups of droplets. Analysis may include detecting the presence/size of each droplet (such as by light scattering) and detecting a signal corresponding to an analyte from the droplet (such as by fluorescence). If droplet size is detected, the signal may be normalized based on the droplet size. Analysis further may include processing results from multiple droplets, to identify components of a complex sample, including the presence and/or identity of material(s) of interest (i.e., analytes) in the complex sample. Such analysis further may include detecting and/or interpreting a presence, amount, and/or activity of a modulator of the sample, including agonists and/or antagonists, and/or determining trends or motifs from the analysis of multiple samples, for example, samples collected at different times and/or from different sources, or before, during, and/or after a treatment or other remedial action.

It may be desirable to separate an enzymatic amplification system such as a PCR-based DNA amplification system into disposable and nondisposable components, for example, by creating a disposable cartridge or other disposable vessel that would prepare and present samples to a nondisposable PCR instrument or other reader. Such a separation could facilitate rapid and low-cost DNA testing and analysis. Although the terms "cartridge" or "disposable cartridge" will be used to reference the disposable portion of the DNA amplification system, the disposable portion generally may take various forms, and need not be rectangular or symmetric in any particular manner or dimension.

A suitable disposable cartridge will be configured to receive a sample and to prepare (or at least partially prepare) the sample for amplification and analysis, prior to PCR thermocycling and amplification. The cartridge may include an interface configured to pass the prepared sample to a nondisposable portion of the system, which generally will be referred to as an "instrument," for subsequent PCR amplification and analysis steps. In some cases, the interface between the cartridge and the instrument also may be configured to transfer various fluids, such as oil and/or aqueous fluid, from the instrument to the cartridge, to "prime" or partially prime the cartridge for sample preparation. In other cases, the cartridge may be partially or entirely pre-primed with fluids, so that fluid transfer from the instrument is not necessary.

A disposable cartridge according to the present disclosure may be configured to generate droplets or packets of droplets, each containing a mixture of sample and reagent, which then may be transported from the disposable cartridge to the related instrument for rapid serial injection into a continuous flow thermal cycler. The cartridge or other disposable vessel then may be removed from the system and discarded. The cartridge may be configured to perform sample preparation steps relatively quickly, as measured by sample throughput from the cartridge to the PCR instrument. For example, a cartridge according to the present disclosure may be configured to perform sample preparation in a time of less than 5 minutes per sample, to achieve throughput of at least 10 samples per hour. The cartridge also may be constructed from and function in conjunction with non-hazardous materials, to minimize environmental impact.

FIG. 1 is a flowchart depicting the steps of a DNA amplification method, generally indicated at 100, that may be performed within or in conjunction with a disposable cartridge of a DNA amplification system according to the present disclosure. The major functions that the disposable cartridge is configured to perform are purification, lysis, reagent mixing, and sample isolation into droplets. However, more generally, any subset or combination of the steps depicted in FIG. 1 may be performed within the cartridge. Alternatively, one or more of the depicted steps, such as sample collection and extraction, may be performed prior to transferring target-containing material into the cartridge, while other steps are performed within the cartridge. Similarly, one or more of the depicted steps, such as droplet generation, may be performed after transferring target-containing material out of the cartridge. Furthermore, the steps depicted in FIG. 1 may be performed in various different orders, only some of which will be described below.

At step 102 of method 100, a sample is collected for subsequent analysis. This is typically done by a medical practitioner, a law enforcement agent, a scientist, or some other person with reason to collect a sample for nucleic acid analysis. The sample may, for example, be collected using a sample collector, such as a swab, a sample card, a specimen drawing needle, a pipette, a syringe, and/or by any other suitable method. Furthermore, pre-collected samples may be stored in wells such as a single well or an array of wells in a plate, may be dried and/or frozen, may be put into an aerosol form, or may take the form of a culture or tissue sample prepared on a slide. Such pre-collected samples then may be obtained and prepared for droplet-based processing in a disposable cartridge. The collected sample typically will include one or more cells, bacteria, viruses, or other material potentially or actually containing a target sequence of nucleotides suitable for PCR amplification.

At step 104, the collected sample is extracted from the sample collector. This may be accomplished, for example, by transferring the sample from the sample collector using a pipette, a syringe, or the like, or by soaking and/or rinsing a sample collector in one or more suitable solutions, such as a digestive buffer solution, a lysis buffer solution, or an appropriate binder-containing solution, among others. Extraction may occur within a chamber of the disposable portion of the PCR system, in which case the sample will be transferred to the cartridge, as indicated at step 106 of method 100, prior to extraction. Alternatively, extraction may occur outside of the cartridge, and the resulting sample or sample-containing solution then may be transferred to the cartridge. In either case, the cartridge may be configured to perform various additional sample preparation steps, as described below.

At steps 108 and 110, the extracted sample, which is now disposed in a sample chamber within the cartridge, is purified and lysed. These steps may be performed at different times, simultaneously, or approximately simultaneously. Furthermore, purification may be performed either before or after lysing, and in some instances two or more separate purification steps may be performed, one before lysing and one after lysing. Purification generally includes some form of filtering to remove unwanted components from the sample while leaving the desired target components relatively unaffected, and lysing generally includes disruption of the sample constituents (e.g., by breaking the cellular membranes) to expose target DNA for amplification, typically involving some form of physical blending or stirring of the sample-containing mixture. For example, lysing may proceed through bulk mixing such as agitation, magnetic stirring, and/or aspiration, or through microfluidic mixing of various types such as forcing the sample through a tortuous path, electromagnetic bombardment, sonication, and/or convection. The fluid containing the contents of the lysed sample may be referred to as a lysate.

Depending on whether a particular purification step is performed before or after lysing, the method of purification may vary. For example, purification prior to lysing may be configured to capture relatively large target-containing material, such as bacteria or other cells. Purification at this stage may, for example, include filtering the sample-containing solution through an aperture-based filter with a characteristic aperture size smaller than the characteristic size of the target-containing cells, to retain the cells within the sample chamber while allowing other, smaller material to be removed. On the other hand, purification after lysing may be configured to capture relatively small target material, such as DNA or partial nucleic acid sequences. Accordingly, post-lysing purification may include filtration through a smaller filter, and/or affinity capture of DNA or other target material. In some cases, such as when purification steps are performed both before and after lysing, two or more different types of filters, including aperture-based filters and/or affinity-based filters, may be used.

At step 112, the partially processed sample (i.e., the lysate) is concentrated. This step is generally accomplished by separating excess fluid in the lysate from the target DNA or DNA-containing material, for example, by filtering, ethanol precipitation, butanol extraction, or affinity capture, among others. In any case, the result of the concentration step is a greater density of target material per unit volume of fluid. Concentration of the sample at this stage may result in a detectable amplified target after relatively fewer PCR amplification cycles than would be necessary without concentration.

At step 114, a PCR reagent mixture including appropriate enzymes and DNA primers is mixed with the sample. These reagent constituents are selected to facilitate DNA amplification of a particular target in conjunction with cyclical temperature changes (i.e., thermocycling). The reagent mixture may be combined with the sample in fluid form, or it may be lyophilized (freeze-dried) and converted into a powder, a pellet, or any other convenient form. To form a lyophilized reagent, suitable stabilizing and/or sedimenting agents may be combined with the PCR enzymes and DNA primers.

Two or more reagents may be mixed with the sample at step 114, to form either a single sample/reagent mixture containing multiple reagents, or multiple mixtures each containing a single reagent. A single mixture containing multiple reagents may, for example, allow screening for multiple targets simultaneously, whereas multiple mixtures each containing a single reagent may be configured for PCR amplification of several different DNA targets, or (when two or more of the mixtures contain the same reagent) to provide experimental control, for instance, by allowing multiple PCR amplification and/or detection techniques to be applied to the same sample/reagent mixture. When multiple sample/reagent mixtures are used, the different mixtures may be separately prepared and/or separately tracked through the system.

At step 116, droplets containing the sample and the reagent are generated, typically in aqueous form within an oil-based emulsion. The generated droplets may contain a mixture of sample and reagent, either activated or not activated (i.e., either requiring or not requiring an additional activation step before PCR amplification begins), or the droplets each may contain sample and reagent that are separated from each other, for example, by a thin membrane, such as an oil membrane. When more than one sample/reagent mixture is present, droplets containing each of the various mixtures may be separately produced and tracked. Common modes of droplet generation include flow focusing, jetting, and shearing. Using these techniques, stable droplets may be created at throughputs of 10-1000 Hz with tunable volumes ranging from 15 picoliters (pL) to 5 nanoliters (nL). Various techniques for generating droplets are known.

At step 118, the droplets produced in step 116 are transferred from the disposable cartridge to a non-disposable instrument portion of the system. As noted above, the droplets may be contained within an emulsion, such as an oil-based emulsion, in which case transferring the droplets will include transferring portions or the entirety of the emulsion. When more than one sample/reagent mixture has been created, the droplets containing each type of mixture may be separately transferred in a continuous or semi-continuous manner, so that each separate droplet type can be separately processed by the instrument portion of the system. Continuous or semi-continuous droplet transfer may allow relatively rapid screening for multiple target DNA segments. Alternatively, or in addition, droplets containing various sample/reagent mixtures may be "tagged" in some manner, such as with a bar code or some other detectable component, in which case different types of droplets may in some instances be transferred to the non-disposable portion of the system together and then tracked or detected individually.

After transfer from the disposable, sample-preparation cartridge portion of the PCR system to the non-disposable instrument portion, thermocycling and analysis will occur. The following examples describe specific exemplary methods and apparatus for receiving a sample in a disposable vessel, such as a cartridge, preparing the sample for PCR amplification, and passing the prepared sample to a reusable instrument portion of a PCR amplification system.

Example A

Disposable Sample Cartridge 1

Figure 2:
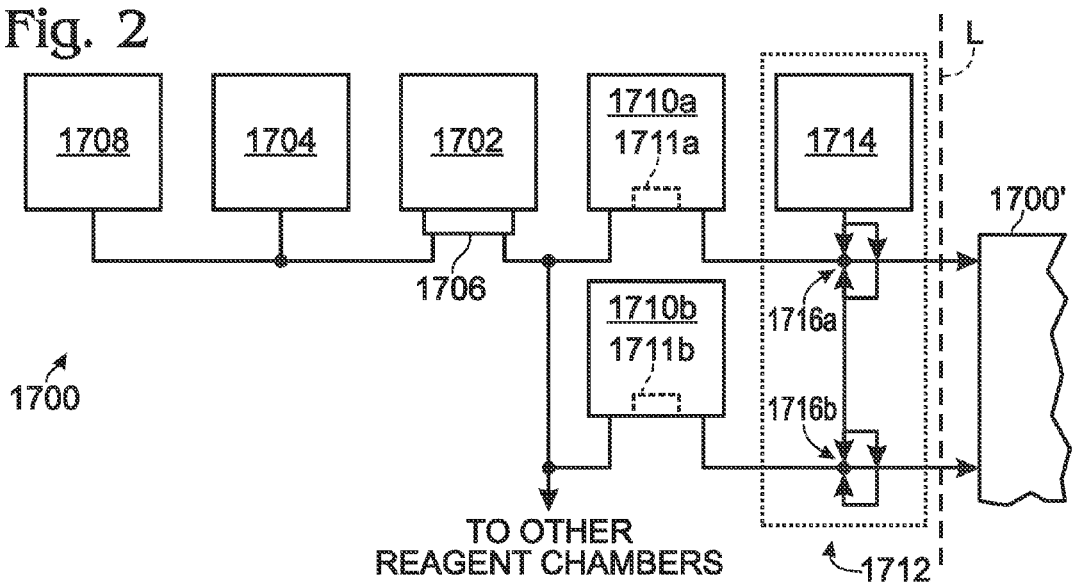
FIG. 2 is a schematic diagram depicting a disposable sample preparation cartridge and suitable fluidic connections between various components of the cartridge, in accordance with aspects of the present disclosure.

This example depicts a disposable sample preparation cartridge and suitable fluidic connections between various components of the cartridge; see FIG. 2.

FIG. 2 is a schematic view of the cartridge, generally indicated at 1700, and suitable fluidic connections between various components of the cartridge. Cartridge 1700 is configured to receive and prepare a target-containing sample for PCR thermocycling and amplification. Preparation of the sample may include some or all of the following steps (not necessarily in this order): purification, lysing, concentration, combination with one or more reagents, and/or generation of droplets suitable for PCR. Droplets containing sample and reagent may be transferred from the cartridge to an instrument, generally indicated at 1700', which is configured to heat the droplets cyclically to facilitate PCR amplification. Dashed line L in FIG. 2 represents the interface between disposable cartridge 1700 and instrument 1700'. This interface may include suitable fluidic connectors, receptors, and the like, to provide a reliable fluidic connection between the cartridge and instrument without significant leakage or contamination.

A sample chamber 1702 of cartridge 1700 is configured to receive a sample. The sample entering chamber 1702 will contain, or at least potentially contain, a target for PCR amplification, such as one or more bacteria, viruses, DNA molecules, and/or other material that contains nucleic acid sequences. For example, the sample may be loaded in the form of eluant that was prepared from a sample collection swab. In some cases, the sample transferred to chamber 1702 may already have been prepared to some extent, for example, by washing, concentrating, and/or lysing, and in other cases the sample may be substantially unprepared or "raw" when it reaches chamber 1702. In any case, sample chamber 1702 may be configured to receive and prepare the sample as described below.

A waste chamber 1704 is fluidically connected to sample chamber 1702, and cartridge 1700 is configured to transfer fluid out of sample chamber 1702, through a filter 1706, and into the waste chamber. Filter 1706 is configured to allow waste products to pass through itself and into the waste chamber, while retaining the PCR target material within the sample chamber. For example, filter 1706 may be a membrane or other similar aperture-type filter with a known characteristic size cutoff. Alternatively, or in addition, the filter may be configured to retain the PCR target within the sample chamber through a suitable form of affinity capture, such as by coating a portion of the sample chamber with an appropriate binding compound. The filter may be used to capture and pre-concentrate the target before the sample is washed, and/or it may be used to retain, additionally concentrate, and/or purify the sample after the sample is washed.

A reservoir chamber 1708 is fluidically connected to sample chamber 1702, and is configured to transfer to the sample chamber a reconstitution fluid, a wash solution, and/or any other fluid suitable for combination with the filtered sample. For example, the fluid transferred from the reservoir chamber may be water, or a buffer solution, such as TE buffer (i.e., a combination of tris(hydroxymethyl)aminomethane, hydrochloric acid, and EDTA), which may remove matrix components that could inhibit downstream PCR amplification. Fluid transferred from the reservoir chamber generally may include any agent configured to separate the target from undesirable components that may have been originally attached to the sample or that may have been used to capture the target when filter 1706 operates through affinity capture.

Sample chamber 1702 also may be configured to lyse the sample. Lysing will typically, but not necessarily, be performed after the target has been washed and/or reconstituted with fluid transferred from reservoir chamber 1708. Lysing may be performed within the sample chamber through mechanical agitation, such as blending, vibrating, shaking, and/or stirring the sample within the chamber, to release nucleic acids from the sample. In some cases, agitation elements, such as discs, rods, and/or small beads may be present in the sample chamber to facilitate lysing. The sample and/or the agitation elements may be agitated by any suitable method, such as manually, through the application of sound waves (i.e., sonication), and/or using magnetic or electromagnetic forces.

Sample chamber 1702 also may be configured to concentrate the target-containing fluid sample. This can be accomplished prior to washing, by transferring some of the original sample-containing fluid from the sample chamber, through the filter, and into the waste chamber. Alternatively, or in addition, concentration can be accomplished by transferring some of the sample-containing fluid into the waste chamber after the sample is washed, while completely or substantially retaining the target nucleic acids within the sample chamber. Concentrating the fluid sample in this manner results in a greater number of target nucleic acids per unit volume of fluid, which can lead to more efficient and faster PCR amplification in subsequent processing steps.

Cartridge 1700 includes one or more reagent chambers. Two reagent chambers 1710a, 1710b are depicted in FIG. 2, but more generally any desired number of reagent chambers, such as five or more, may be utilized. Each reagent chamber contains reagents, such as primers, polymerase, and appropriate enzymes, configured to react with a particular target nucleic acid sequence and to undergo PCR amplification if the target is present in the sample. Typically, the reagents will be pre-loaded into each reagent chamber during the cartridge manufacture, although in some embodiments the reagents may be loaded by a user or transferred from a related PCR instrument.

The reagents may be stored in or introduced into the reagent chambers in any suitable manner. For example, the reagents may take the form of lyophilized pellets 1711a, 1711b depicted in FIG. 2, or a coating (not shown) applied to a portion of the interior wall of each reagent chamber. Alternatively, a reagent coating may be applied to a stir element disposed within the reagent chamber, and/or to a plunger used to vary transfer fluid into and out of the reagent chamber. The reagent chambers of FIG. 2 are fluidically connected in parallel with the sample chamber, so that each reagent chamber can separately receive a portion of the filtered, lysed sample-containing solution, without cross-contamination. One or more stir elements (not shown) may be included in each reagent chamber to facilitate mixing the sample with the pre-loaded reagents. When stir elements are included in the reagent chambers, they may operate manually, through sonication, or using magnetic or electromagnetic forces, in a manner similar to the operation of the agitation elements used for lysing in the sample chamber.

Reagent chambers 1710a and 1710b are each fluidically connected to a droplet generator, generally indicated at 1712. Droplet generator 1712 is configured to generate discrete micro-volume droplets, each containing all of the ingredients for subsequent nucleic acid amplification via PCR. In general, droplet generator 1712 is configured to generate one or more water-in-oil emulsions, although other types of emulsions, such as oil-in-water, water-in-oil-in-water, and so forth are also possible.

Parallel fluid connections lead to droplet generator 1712 from reagent chambers 1710a and 1710b. A common oil reservoir 1714 is configured to transfer oil along the fluid paths indicated, so that oil arrives at each of intersection points 1716a and 1716b from two separate directions. At the intersection points, sample-containing solution arrives from the respective reagent chambers and combines with the oil from the oil reservoir to form water-in-oil droplets. The generated droplets are then transferred across interface L and into instrument 1700'. Each sample/reagent mixture may be transferred either serially or in parallel to droplet generator 1712. Other droplet generator configurations may be suitable, as described below.

After droplets have been generated, system 1700 is configured to facilitate transfer of the droplets through interface L to instrument 1700'. This transfer may be accomplished through the use of suitable fluidic tubing, capillaries, pumps, valves, and/or the like, which may be configured to transfer droplets to the instrument either as parallel streams or in separate (serial) batches, each of which contains droplets that include a specific reagent. The droplets then may be transferred through a multi-port valve and introduced into a thermocycler for PCR amplification.

Example B

Disposable Sample Cartridge 2

This example describes an exemplary disposable cartridge that is suitable for performing some or all of the sample preparation steps described above; see FIGS. 3-5.

FIG. 3 is an isometric view of an interior portion of the exemplary cartridge, generally indicated at 1720. The cartridge is configured to interface with an instrument (not shown), so that prepared samples can be transferred to the instrument, generally in the form of a water-in-oil emulsion, for PCR amplification and analysis. In addition to the interior portion depicted in FIG. 3, cartridge 1720 also may include a suitable exterior housing (not shown) disposed around some or the entirety of the interior portion. The exterior housing may be configured to protect the interior portion and may be shaped to facilitate storage and/or transportation of multiple cartridges.

Cartridge 1720 includes an upper section 1722 and a lower section 1724, which are configured to fit together to form the interior portion of the cartridge. For clarity, the upper and lower sections are separated by a slight gap in the drawings. These sections may be manufactured by any suitable method, such as by injection molding a thermoplastic material. The upper and lower sections may be bonded together in any suitable manner, for example, with connecting pins (or similar connectors), with an adhesive, and/or by thermal curing, to maintain the structural integrity of the assembled cartridge.

FIGS. 4 and 5 are side elevation and top views, respectively, of the interior portion of cartridge 1720. These drawings, together with FIG. 3, show that the cartridge includes a number of discrete chambers. These chambers are fluidically connected by a fluid path, which is generally indicated at 1726 in FIG. 5. Fluid path 1726 may result from joining complementary grooves formed within each of sections 1722 and 1724, so that a closed fluid path results when the sections are joined together. The grooves of each section may, for example, have an approximately hemispherical profile, so that the grooves form a substantially cylindrical fluid path when the upper and lower sections of the cartridge are assembled. In other embodiments, the grooves may have other shapes, such as rectangular, and the allocation of the total cross section between the upper and lower sections may vary.

A sample chamber 1728 of cartridge 1720 is configured to receive a sample that contains (or potentially contains) a target nucleic acid sequence. The sample may be transferred into the sample chamber as a fluid, or it may be placed in the chamber attached to a swab or some other suitable sample collection medium. The sample chamber can be constructed to have any desired shape, such as the cylindrical shape depicted in FIGS. 3 and 4, and any desired volume, such as a volume in the range of 200 microliters (μL) to 2 milliliters (mL). The volume of the sample chamber may depend in part on the number of separate nucleic acid targets for which the cartridge is configured to test, as described below.

Sample chamber 1728 may include a filter 1730. The filter will typically be disposed near or below the bottom surface of the sample chamber. Filter 1730 may be a size-exclusion filter configured to prevent passage of material larger than a particular preselected size. For example, to prevent passage of bacteria having a characteristic size of 600 nanometers (nm), the filter may be a membrane with a characteristic cutoff size of 200-400 nm. To prevent passage of other material, the filter may be chosen to have a different characteristic cutoff size, which is selected based on the material to be filtered. Membrane filtration based on size fractionation is a simple, yet effective method of capturing target cells. Once captured, the cells can be washed to remove potential PCR inhibitors that are soluble or below the size cutoff of the membrane.

Alternatively, filter 1730 may operate through affinity capture (i.e., by attracting and/or chemically binding one or more target molecules), or by solid phase extraction, such as chemical precipitation. However, membrane filtration may have certain advantages over solid phase extraction, including a reduced number of processing steps, no hazardous reagents, fast processing times, and the potential for simultaneous concentration and purification of the target organisms, as described below.

The sample chamber also may include one or more lysing elements, such as a stirring disc 1732 and/or lysis beads 1734; see FIGS. 3 and 4. These elements are generally configured to facilitate lysis of a fluid in the sample chamber, through agitation of the sample to release nucleic acids by breaking down surrounding material (such as cellular material). The lysing disc 1732 or other similar stirring element will typically be disposed toward the bottom of, but within, the sample chamber. Lysis beads 1734, which can take the form of beads of any desired material and diameter, such as glass beads with diameters in the range of 70-700 μm, are configured to further facilitate lysis by colliding with and disrupting material within the agitated fluid of the sample chamber.

Agitation of stirring disc 1732, which also can take the form of a rod or any other suitable shape, may be provided by magnetic or electromagnetic forces. For example, the stirring disc may be sufficiently magnetic to respond to a changing magnetic field applied to the sample chamber. Thus, variations in the applied magnetic field can cause the stirring disc to spin and/or tumble, resulting in agitation of the fluid within the sample chamber. A variable magnetic field may be provided, for example, by a single low-cost driver located on the related PCR instrument. The driver may be configured to drive the lysing elements within one, several, and/or a multitude of sample chambers simultaneously. Because the lysing elements are contained within the sample chamber and because the magnetic driver may be configured to act across a plurality of sample chambers, lysing within cartridge 1720 does not require a special interface between the disposable cartridge and the related instrument. This configuration provides a high degree of amenability to integration and automation within a low-cost single-use cartridge.

Sample chamber 1728 is configured to receive one or more fluids, such as a wash and/or a reconstitution solution, from a reservoir chamber 1736. When the sample transferred to the sample chamber is attached to a medium, such as a swab, fluid from the reservoir chamber may be used to reconstitute the sample into fluidic form. Fluid from the reservoir chamber also may be used to purify a sample, such as bacteria, by washing the sample with a buffer solution. The fluid in reservoir chamber 1736 may be provided with the cartridge, supplied by a user, and/or transferred to the cartridge from an instrument to which the cartridge attaches. In any case, fluid may be transferred from reservoir chamber 1736 to sample chamber 1728 along fluid path 1726, which connects the two chambers. This connection can be seen, for example, in FIG. 5, which is a top view of cartridge 1700. Fluid transferred from the reservoir chamber to the sample chamber passes through filter 1730, so that the fluid is filtered before entering the sample chamber.

Cartridge 1720 also includes a waste chamber 1738. The waste chamber is configured to receive waste material, such as nucleic acid fragments and other waste material either introduced to the sample chamber with the sample or fragmented during lysing, from the sample chamber. Waste chamber 1738 is fluidically connected to sample chamber 1728 through fluid path 1726, which passes through filter 1730. Accordingly, fluid and fragmentary waste products may be transferred from the sample chamber to the waste chamber, while target material having a characteristic size (or chemical affinity) suitable for capture by the filter will be retained within the sample chamber.

For example, sample-containing solution may be purified prior to lysing by filtering the fluid through filter 1730 and into waste chamber 1738. The fluid in the sample chamber then may be replenished from reservoir chamber 1736, as described previously. Similarly, sample-containing solution may be purified and/or concentrated after lysing, again by filtering the fluid through filter 1730 and into waste chamber 1738. The steps of purification, concentration, and fluid replenishment may be repeated any desired number of times by transferring fluid from the sample chamber to the waste chamber and from the reservoir chamber to the sample chamber.

FIGS. 3-5 depict five separate reagent chambers 1740a, 1740b, 1740c, 1740d and 1740e within cartridge 1720. In general, any desired number of reagent chambers, from one, two, three, four, five, six, seven, eight, nine, ten, or more, up to an arbitrarily large number, may be provided (both in this embodiment and other disposable cartridges shown herein). Each reagent chamber is configured to receive sample-containing fluid from the sample chamber, and to allow the combination of the sample-containing fluid with a particular reagent mixture. Sample-containing fluid can be transferred from the sample chamber to the reagent chambers along fluidic path 1726, which connects the sample chamber to each of the reagent chambers in parallel, as can be seen in FIG. 5.

Each reagent mixture may include, for example, primers, polymerase, and/or enzymes suitable for PCR amplification of a particular nucleic acid sequence. The reagent mixtures in two or more of reagent chambers 1740 may be the same or substantially similar (for example, to allow for experimental control), or each reagent mixture may be substantially different, to search for multiple different target nucleic acid sequences.

The reagent mixtures of cartridge 1720 are depicted as lyophilized pellets 1742a, 1742b, 1742c, 1742d, and 1742e disposed at the bottom of the associated reagent chambers; see FIG. 5. However, in general the reagent mixtures can be provided in any suitable form, such as within a fluid, as a lyophilized powder (either loose or shaped into a form other than a pellet), or as a coating applied to the interior surface of each reagent chamber, among others. Furthermore, the reagent mixtures may be supplied with the cartridge, supplied by a user, or transferred to the cartridge from a PCR instrument to which the cartridge is connected.

Cartridge 1720 also includes an oil chamber 1744, which is fluidically connected to each of reagent chambers 1740a, 1740b, 1740c, 1740d, and 1740e. Oil chamber 1744 is configured to supply the oil needed to produce a water-in-oil emulsion containing droplets of sample and reagent fluid. More specifically, oil can pass from chamber 1744 to a plurality of droplet generation regions 1745a, 1745b, 1745c, 1745d, and 1745e, each corresponding to and fluidically connected with one of the reagent chambers. Each droplet generator is configured to generate droplets of a particular sample/reagent mixture suspended in an oil background.

Specifically, as depicted in FIG. 5, oil in cartridge 1720 passes from oil chamber 1744 down a plurality of fluid pathways. These include a pair of oil pathways corresponding to each droplet generator and configured to intersect with a fluid pathway from one of the reagent chambers, to create water-in-oil droplets. The generated droplets then may pass through interface components, such as a plurality of capillary connectors 1746a, 1746b, 1746c, 1746d, and 1746e. The capillary connectors are configured to transfer fluid to a plurality of corresponding capillaries 1748a, 1748b, 1748c, 1748d, and 1748e, which are configured to interface with instrument 1700' (see, e.g., FIG. 2).

Example C

Exemplary Hydraulic Mechanisms

This example describes aspects of two exemplary hydraulic mechanisms suitable for controlling fluid motion between the various chambers of a disposable cartridge; see FIGS. 6 and 7.

FIG. 6 schematically illustrates aspects of a two-chamber hydraulic mechanism, generally indicated at 1760, that is suitable for controlling fluid motion between the various chambers of a disposable cartridge, such as cartridges 1700 or 1720 described above. Each side of FIG. 6 depicts two fluid chambers 1762 and 1764. Each chamber is equipped with a plunger 1766, and a fluid 1768 is partially disposed within each chamber. In the left-hand portion of FIG. 6, the majority of the fluid is disposed in chamber 1764, and in the right-hand portion of FIG. 6, the majority of the fluid is disposed in chamber 1762. A connecting fluid pathway 1770 is provided between chambers 1762 and 1764, which allows fluid 1768 to pass between the chambers.

Fluid motion between chambers will occur when unequal forces are applied to the two plungers 1766, causing one of the plungers to move down while the other moves up. Such forces will typically be applied by a force actuator, such as a piston or a push rod, which will be contained within or otherwise integrated with an instrument configured to receive a disposable sample preparation cartridge. In this manner, fluid can be transferred between any of the previously described chambers of a disposable cartridge in a controlled manner.

More specifically, motions of plungers 1766 may be controlled directly by a user and/or by an instrument configured to receive and interact with the cartridge containing the plungers. For example, a user might manually load a sample or a sample-containing fluid into one of chambers 1762 or 1764 (which would therefore be considered a sample chamber), and then insert a plunger 1766 into the chamber, sealing the sample or sample-containing fluid within the chamber. Fluid then may be transferred hydraulically into and out of the sample chamber by depressing the appropriate plunger either manually or automatically.

Automatic plunger motions may be controlled by a processor programmed to transfer fluids between chambers of the system in a predetermined manner. For instance, if hydraulic mechanism 1760 is incorporated into cartridge 1700, then instrument 1700' may include force actuating structures complementary to the plungers of the hydraulic mechanism, such as pistons, push rods or the like. These force actuators may be configured to depress the associated plungers at particular times, in a particular order, or in response to signals sent to the instrument by a user.

FIG. 7 schematically depicts a three-chamber hydraulic mechanism, generally indicated at 1780, which is similar to two-chamber mechanism 1760 of FIG. 6. Fluid chambers 1782, 1784, and 1786 each include a plunger 1787. A fluid 1788 is partially disposed within each chamber, and the chambers are fluidically connected by a fluid pathway 1790. Accordingly, fluid will be transferred from one chamber to one or both of the other chambers when plungers 1787 are moved appropriately. For example, fluid from chamber 1786 can be transferred to chambers 1782 and 1784 by depressing the plunger of chamber 1786 and simultaneously raising the plungers of chambers 1782 and 1784.

If the chambers all have the same size and geometry, then to transfer an equal amount of fluid from chamber 1786 to chambers 1782 and 1784, each of the plungers of chambers 1782 and 1784 would be raised at half the rate with which the plunger of chamber 1786 is depressed. Alternatively, the chambers may have different sizes and/or shapes, in which case the plunger motions would be suitably modified to achieve equal fluid transfer from one chamber to the other chambers. Furthermore, fluid from one chamber can be divided among two or more other chambers according to any desired ratio of volumes, by controlling the motions of the various plungers.

Plungers according to the present disclosure may include a locking mechanism. The locking mechanism of a particular plunger may be configured to lock the plunger into a particular position, to avoid undesirable transfer of fluid to or from a particular chamber. For example, a plunger associated with a waste chamber may include a locking mechanism configured to lock the plunger in place when the plunger reaches an upper (retracted) position, corresponding to a maximum volume of fluid within the waste chamber. This can prevent waste fluid from unintentionally being transferred back into another chamber, such as a sample chamber or a reservoir chamber, after waste has been removed from a sample.

A suitable plunger locking mechanism can take various forms, each having the common property that the mechanism prevents particular unwanted plunger motions. For example, a suitable locking may include a mechanism integrated with the plunger itself, such as a spring-biased tab or the like (not shown) that snaps into place when the plunger reaches a certain position, preventing subsequent downward plunger motions. Alternatively, the locking mechanism may be associated with the instrument configured to receive the disposable cartridge, in which case the locking mechanism may include programming a controller to avoid causing downward motions of a particular plunger under certain circumstances.

Plungers according to the present disclosure also may be configured to limit or eliminate leaks. For example, as depicted in FIG. 7, plungers 1787 may include both a lower seal 1790 and an upper seal 1792, attached to a common shaft 1794 and separated by a desired distance. Seals 1790 and 1792 typically will take the form of o-rings or similar structures configured to fit in a substantially fluid-tight manner within the inner circumference of the associated chamber. Thus, as FIG. 7 depicts (see chamber 1786), any residual fluid 1788 that passes the lower seal as a plunger is depressed will still be trapped within the associated chamber by the upper seal.

Example D

Exemplary Droplet Generators

This example describes various exemplary droplet generation configurations that may be suitable for generating water-in-oil droplets containing a mixture of sample and reagent; see FIGS. 8A-8F. The generated droplets then may be transported to a thermocycling instrument for PCR amplification. Each depicted configuration is compatible with continuous production of oil phase emulsions and with both pressure-controlled and positive displacement pumping. A droplet generator or droplet generation configuration according to the present disclosure may be connected to a pressure/pump source located on a complementary PCR instrument, or may include any pumps and/or pressure sources needed to facilitate droplet generation.

Each depicted droplet configuration in FIGS. 8A-8F may be capable of high-throughput droplet generation (~1,000 droplets per second) in a disposable device, such as a cartridge. Each configuration may be constructed by injection molding two layers of material that fit together to form fluid channels, such as cylindrical channels formed by complementary hemispherical grooves. The fluid channels of the droplet generation configurations depicted in FIGS. 8A-8F may have varying channel depths, such as 50, 100, 150, 200, or 250 μm, among others.

FIG. 8A depicts a 3-port cross droplet generation configuration 1800 wherein oil from a first fluid well (or chamber) 1802 is transferred through two similar branches of a fluid channel section 1804. The oil from well 1802 intersects with aqueous fluid from a second fluid chamber 1806, which is transferred along a fluid channel section 1808 to an intersection area generally indicated at 1810. The oil from well 1802 arrives at intersection 1810 from two different and substantially opposite directions, whereas the aqueous solution arrives at the intersection along only a single path that is substantially perpendicular to both directions of travel of the arriving oil. The result is that at intersection 1810, aqueous droplets in an oil background (i.e., a water-in-oil emulsion) are produced and transferred along a fluid channel section 1812 to a third chamber 1814, where the emulsion can be temporarily stored and/or transferred to a thermocycling instrument.

FIG. 8B depicts a configuration 1815 that is similar in most respects to droplet generation configuration 1800 depicted in FIG. 8A. Specifically, in droplet generation configuration 1815, oil from a first fluid chamber 1816 is transferred through two similar branches of a fluid channel section 1818. Fluid channel sections 1818 intersect with a fluid channel section 1822 that transfers aqueous fluid from a second fluid chamber 1820, at an intersection area generally indicated at 1824. As in configuration 1800, the oil from chamber 1816 arrives at intersection 1810 from two different directions, but unlike in configuration 1800, the oil does not arrive from substantially opposite (antiparallel) directions. Rather, channel sections 1818 each intersect channel section 1822 at a non-perpendicular angle, which is depicted as approximately 60 degrees in FIG. 8B. In general, configuration 1815 may include oil fluid channels that intersect an aqueous fluid channel at any desired angle or angles. Oil flowing through channel sections 1818 and aqueous solution flowing through channel section 1822 combine to form a water-in-oil emulsion of aqueous droplets suspended in an oil background. As in the case of configuration 1800, the droplets then may be transferred along a fluid channel section 1826 to a third fluid chamber 1828, for storage and/or transfer to a thermocycling instrument.

Figure 8C:
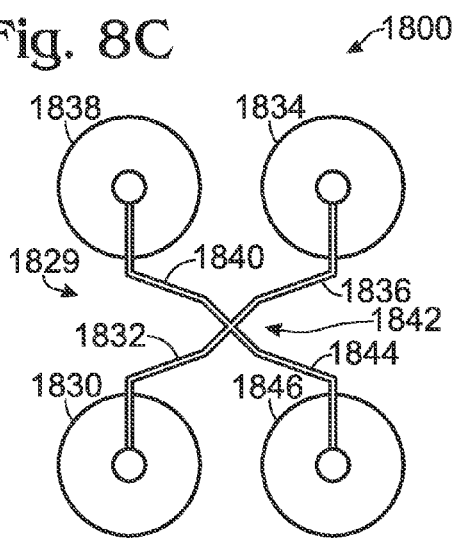

FIG. 8C depicts a four-port droplet generation configuration 1829 that includes two separate oil wells or chambers. A first oil chamber 1830 is configured to store oil and transfer the oil through a fluid channel section 1832 toward a channel intersection point generally indicated at 1842. A second oil chamber 1834 is similarly configured to store and transfer oil toward the intersection point through a fluid channel section 1836. An aqueous fluid chamber 1838 is configured to store aqueous fluid, such as a sample/reagent mixture, and to transfer the aqueous fluid through fluid channel section 1840 toward intersection point 1842. When the oil traveling through fluid channel sections 1832 and 1836 intersects with the aqueous fluid traveling through fluid channel section 1840, a water-in-oil emulsion of aqueous droplets suspended in oil is generated. Although fluid channel 1840 is depicted as intersecting with each of fluid channels 1832 and 1836 at a perpendicular angle, in general the channels may intersect at any desired angle, as described previously with respect to droplet generation configuration 1815 of FIG. 8B. The emulsion generated at intersection 1842 travels through outgoing fluid channel section 1844 toward an emulsion chamber 1846, where the emulsion may be temporarily held for transfer to an instrument, such as a thermocycling instrument.

Figure 8D:
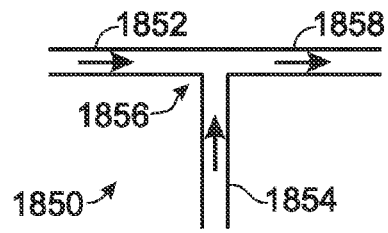
Figure 8F:
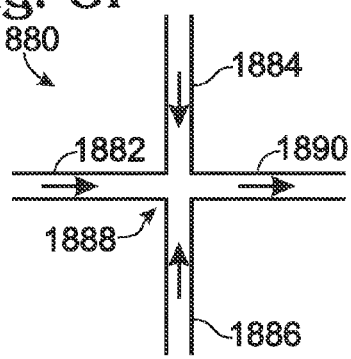
Figure 8E:
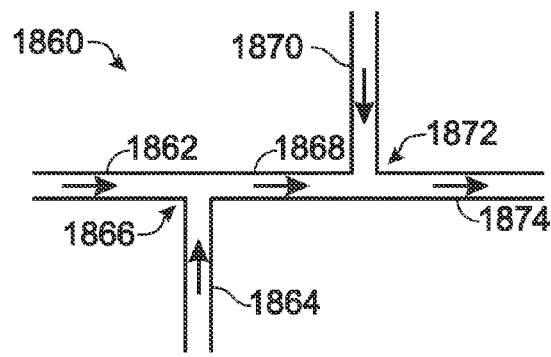

FIGS. 8D-8F schematically depict fluid channel intersection regions of several other possible droplet generation configurations, in which the arrows within the depicted fluid channels indicate the direction of fluid flow within each channel. Although fluid chambers for receiving and/or storing oil, water, and any generated emulsion are not depicted in FIGS. 8D-8F, these chambers or at least some source of oil and aqueous fluid would be present in a cartridge containing any of the depicted configurations. The fluid channels and any associated chambers may be formed by any suitable method, such as injection molding complementary sections of thermoplastic as described previously.

FIG. 8D depicts a "single T" configuration 1850 in which oil traveling in an oil channel 1852 intersects with aqueous fluid traveling in an aqueous channel 1854 at fluid channel intersection 1856, to produce a water-in-oil emulsion that travels through outgoing fluid channel 1858. This configuration differs from those of FIGS. 8A-8C in that oil arrives at the oil/water intersection from only a single direction. Accordingly, droplets may be formed by a slightly different physical mechanism than in configurations where oil arrives from two directions. For example, droplets formed in the single T configuration of FIG. 8D may be formed primarily by a shear mechanism rather than primarily by a compression mechanism. However, the physics of droplet formation is not completely understood and likely depends on many factors, including the channel diameters, fluid velocities, and fluid viscosities.

FIG. 8E depicts a "double T" configuration 1860 in which oil traveling in an oil channel 1862 intersects with aqueous fluid traveling in a first aqueous channel 1864 at a first intersection 1866, to produce a water-in-oil emulsion that travels through intermediate fluid channel 1868. Channel 1868 intersects with a second aqueous channel 1870 at a second intersection 1872, to generate additional water-in-oil droplets within the emulsion. All of the generated droplets then travel through outgoing fluid channel 1874. This configuration again differs from those of FIGS. 8A-8C in that oil arrives at the oil/water intersections from only a single direction. In addition, configuration 1860 differs from single T configuration 1850 depicted in FIG. 8D due to the presence of two oil/water intersections. This may result in a greater density of droplets in the water-in-oil emulsion generated by configuration 1860 than in the emulsion generation by configuration 1850, which includes only one oil/water intersection.

FIG. 8F depicts a droplet generation configuration 1880 in which oil traveling in an oil channel 1882 intersects with aqueous fluid traveling in first and second aqueous channels 1884 and 1886 at an intersection 1888. In this configuration, the aqueous fluid arrives at the intersection from two opposite directions, both of which are substantially perpendicular to the direction of travel of the oil in channel 1882. More generally, the aqueous fluid can intersect with the oil at any desired angles. Depending on at least the sizes of the various channels, the flow rates of the oil and the aqueous fluid, and the angle of intersection of the aqueous fluid channels with the oil channel, a configuration of this type may be suitable for producing either an oil-in-water emulsion or a water-in-oil emulsion. In either case, the emulsion will travel away from intersection 1888 through outgoing fluid channel 1890.

Example E

Disposable Sample Cartridge 3

Figure 9:
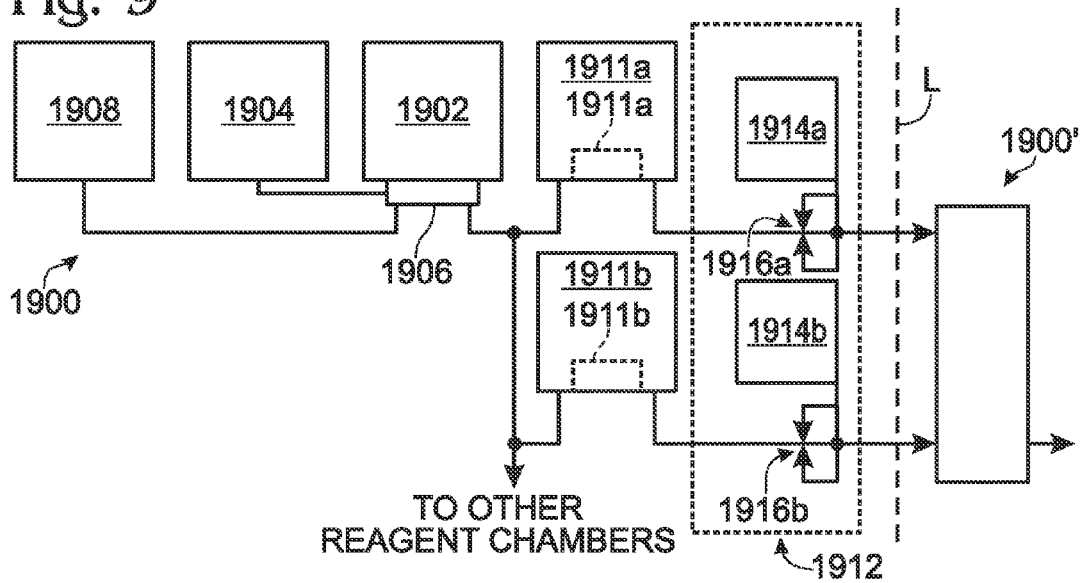
FIG. 9 is a schematic diagram depicting another disposable sample preparation cartridge and suitable fluidic connections between various components of the cartridge, in accordance with aspects of the present disclosure.
Figure 10:
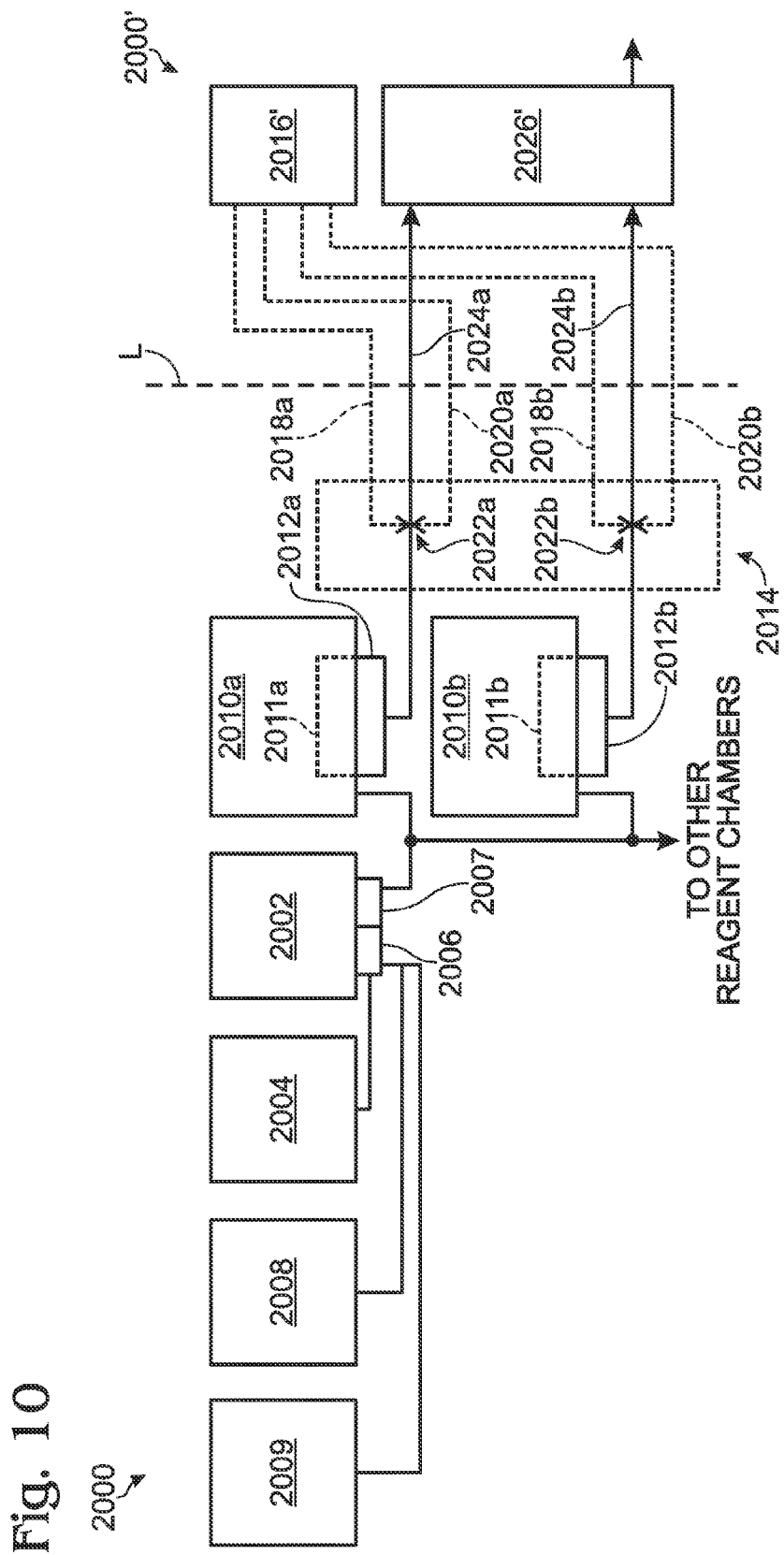
FIG. 10 is a schematic diagram depicting still another disposable sample preparation cartridge (left), portions of a complementary PCR instrument (right), and suitable fluidic connections among and between various components of the cartridge and instrument, in accordance with aspects of the present disclosure.
Figure 11:
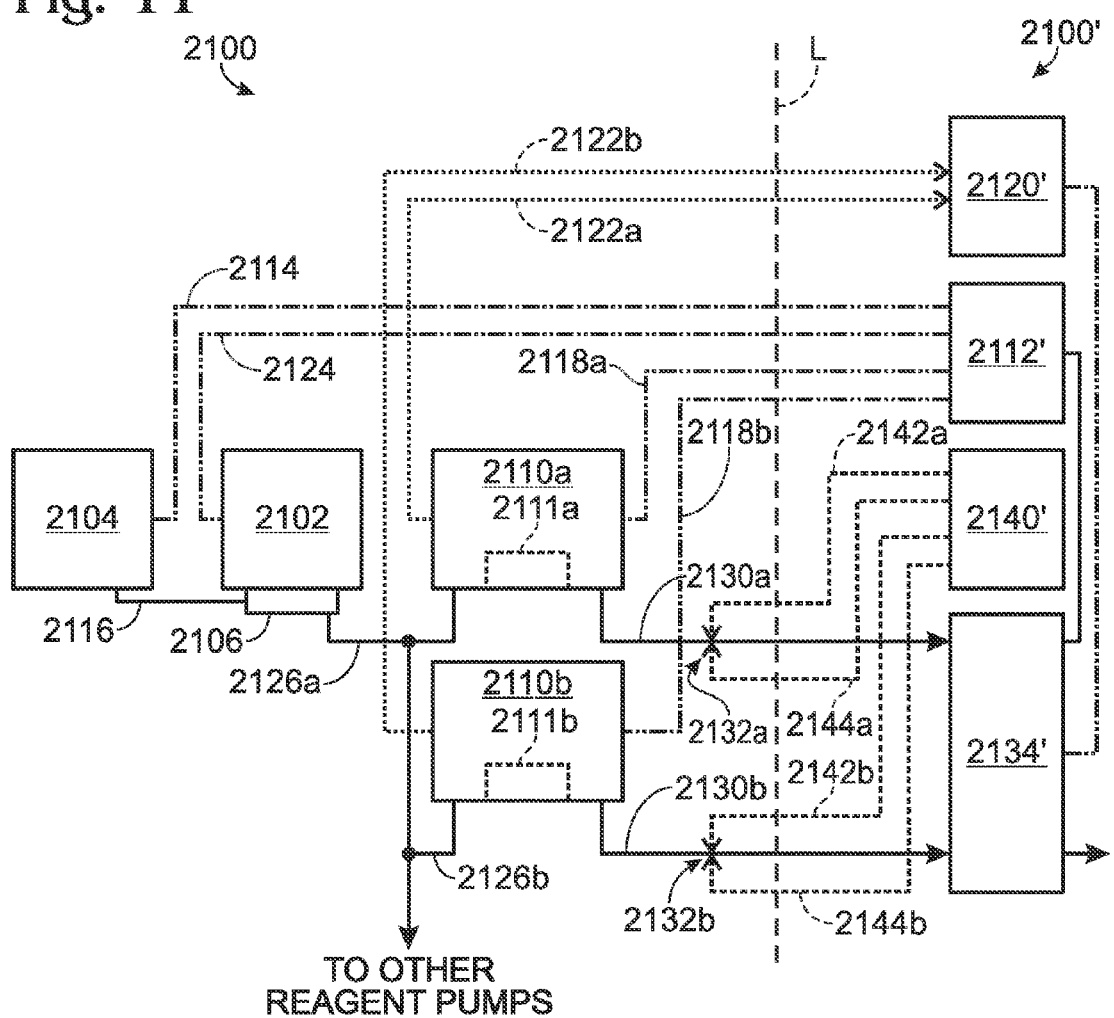
FIG. 11 is a schematic diagram depicting still another disposable sample preparation cartridge (left), portions of a complementary PCR instrument (right), and suitable fluidic connections among and between various components of the cartridge and instrument, in accordance with aspects of the present disclosure.

This example describes aspects of three alternative disposable sample preparation cartridges; see FIGS. 9-11.

FIG. 9 is a schematic diagram depicting another disposable sample preparation cartridge, generally indicated at 1900, and suitable fluidic connections between various components of the cartridge. Cartridge 1900 is configured to receive and prepare a target-containing sample for PCR thermocycling and amplification, and is substantially similar to cartridge 1700 depicted in FIG. 2 in many respects. Accordingly, cartridge 1900 includes a sample chamber 1902, a waste chamber 1904, a filter 1906, a reservoir chamber 1908, and reagent chambers 1910*a*, 1910*b* that may be pre-loaded with reagents 1911*a*, 1911*b*. These components are similar to their counterparts in cartridge 1700, and will not be described again in detail. As in the case of cartridge 1700, any desired number of reagent chambers, such as five or more, may be provided in cartridge 1900.

Cartridge 1900 also includes a droplet generator, generally indicated at 1912, which differs slightly from droplet generator 1712 of cartridge 1700. Specifically, droplet generator 1912 includes two separate oil reservoirs 1914*a*, 1914*b* corresponding to, and separately connected to, the two different reagent chambers. Thus, oil reservoir 1914*a* transfers oil to intersection point 1916*a*, where the oil combines with aqueous fluid from reagent chamber 1910*a* to form a first water-in-oil emulsion of sample/reagent droplets, and oil reservoir 1914*b* transfers oil to intersection point 1916*b*, where the oil combines with aqueous fluid from reagent chamber 1910*b* to form a second water-in-oil emulsion of sample/reagent droplets. Both emulsions then may be transferred to an instrument 1900' for thermocycling. In comparison to cartridge 1800, providing separate oil reservoirs and oil channels in the manner of cartridge 1900 may reduce any chance of cross-contamination between reagents from the separate reagent chambers.

FIG. 10 is a schematic diagram depicting still another disposable sample preparation cartridge, generally indicated at 2000, and suitable fluidic connections between various components of the cartridge. Like cartridges 1700 and 1900 depicted in FIGS. 2 and 9, respectively, cartridge 2000 is configured to receive and prepare a target-containing sample for PCR thermocycling and amplification. Cartridge 2000 includes a sample chamber 2002, a waste chamber 2004, a first filter 2006, and a first reservoir chamber 2008, which are similar to their counterparts in cartridge 1700, and will not be described again in detail.

Cartridge 2000 also includes a second reservoir chamber 2009. Filter 2006 is disposed between sample chamber 2002 and each of reservoir chambers 2008 and 2009, and serves to retain the target-containing sample in the sample chamber as fluid is transferred into and out of the sample chamber. As in the previously described exemplary cartridges, reconstitution and/or wash fluid will typically be transferred into the sample chamber from one of the reservoir chambers, and waste fluid will typically be transferred out of the sample chamber into the waste chamber.

First and second reservoir chambers 2008 and 2009 are provided so that the sample in the sample chamber may be reconstituted and/or washed twice. For example, a reconstitution solution may be transferred into the sample chamber from reservoir chamber 2008, after which the sample may be lysed as has been described previously. Waste fluid then may be transferred from the sample chamber into waste chamber 2004, while the target material is retained in the sample chamber. Next, a wash solution may be transferred into the sample chamber from reservoir chamber 2009, and waste fluid again may be transferred from the sample chamber into the waste chamber. Providing two reservoir chambers and two reconstitution/wash steps may result in a sample that contains relatively few impurities and thus a relatively high fraction of target material.

A second filter 2007 is disposed between sample chamber 2002 and reagent chambers 2010*a*, 2010*b*. The reagent chambers may be pre-loaded with reagents 2011*a*, 2011*b*, and both the reagent chambers and the reagents are similar to their previously described counterparts. Filter 2007 is configured to allow passage of target nucleotide material from the sample chamber to the reagent chambers, while preventing passage of larger material, such as lysis beads or large waste material that remains in the sample chamber after purification and lysis. As in the case of cartridges 1700 and 1900, any desired number of reagent chambers, such as five or more, may be provided in cartridge 2000.

Alternatively, or in addition, to filter 2007, additional filters 2012*a*, 2012*b* may be provided with reagent chambers 2010*a*, 2010*b*, and similar additional filters may be provided with each additional reagent chamber. These additional filters may serve a similar purpose as filter 2007, i.e., preventing relatively large waste material, such as lysis beads, from proceeding further through the cartridge. Providing both a second filter 2007 and additional filters 2012*a*, 2012*b* may result in a relatively more pure sample/reagent mixture transferred from the reagent chambers toward a droplet generation portion of the cartridge.

Cartridge 2000 includes a droplet generator, generally indicated at 2014, which is configured to generate a water-in-oil emulsion corresponding to each reagent chamber. Unlike the previously described cartridges, however, the oil for the emulsion is supplied by a related instrument 2000' rather than from within the cartridge. To describe the interaction between the cartridge and the instrument, primed reference numbers will be used to represent components of instrument 2000', whereas unprimed reference numbers will continue to be used to reference components of cartridge 2000.

To supply oil to cartridge 2000, an oil reservoir 2016' within instrument 2000' transfers the oil along oil lines 2018a, 2020a, to generate droplets corresponding to reagent chamber 2010a. The oil intersects aqueous solution from reagent chamber 2010a at an intersection region 2022a, to generate droplets containing a sample/reagent mixture that may be transferred into instrument 2000' for thermocycling. Similarly, oil reservoir 2016' supplies oil along lines 2018b, 2020b to generate droplets corresponding to reagent chamber 2010b at an intersection region 2022b, and oil reservoir 2016' (or additional reservoirs, not shown) may be configured to supply oil to generate droplets corresponding to any desired number of additional reagent chambers that are included in cartridge 2000.

Sample/reagent droplets generated at regions 2022a, 2022b, and at any other additional droplet generation intersection regions of cartridge 2000, all may be transferred through corresponding fluidic pathways 2024a, 2024b (and so forth) to a multi-port valve 2026' of instrument 2000'. Valve 2026' may, for example, be configured to receive droplets from multiple fluidic input channels, and to transfer the droplets to a thermocycling region of the instrument in any desired manner, such as in controlled batches of one type of sample/reagent droplets at a time.

FIG. 11 is a schematic diagram depicting yet still another disposable sample preparation cartridge, generally indicated at 2100, and suitable fluidic connections between various components of the cartridge. Like the previously described cartridges, cartridge 2100 is configured to receive and prepare a target-containing sample for PCR thermocycling and amplification. Cartridge 2100 includes several of the features of the other cartridges, including a sample chamber 2102, a waste chamber 2104, a filter 2106, and reagent chambers 2110a, 2110b (plus any desired number of additional reagent chambers). These components are similar to their previously described counterparts, and will not be described again in detail.

Cartridge 2100 is configured to be inserted into or otherwise interact with a related PCR instrument 2100', shown to the right of interface line L in FIG. 11. In this case, instrument 2100' supplies substantially all of the working fluids, other than the sample or sample-containing fluid, to the cartridge. In other words, instrument 2100' is configured to prime cartridge 2100 with fluids. As in the case of the description relating to FIG. 10, primed reference numbers will be used in the description of FIG. 11 to represent components of instrument 2100', whereas unprimed reference numbers will continue to be used to reference components of cartridge 2100.

A reservoir pump 2112' of instrument 2100' may be equipped with a selector valve or similar mechanism to allow fluid to be selectively transferred from the reservoir pump through the various fluid channels leading from the pump. After cartridge 2100 is placed in a secure position within or adjacent to instrument 2100', so that a substantially fluid tight seal is formed, the reservoir pump pumps fluid into fluid channel 2114 toward waste chamber 2104, which is typically empty of fluid when the cartridge is connected to the instrument. Reservoir pump 2112' continues pumping fluid into channel 2114 until the fluid fills channel 2114 and proceeds through channel 2116 to fill filter 2106. The reservoir pump then stops pumping fluid into channel 2114 and begins pumping fluid into channel 2118a toward reagent chamber 2110a, continuing until fluid fills channel 2118a. During operation of reservoir pump 2112', a waste pump 2120', which is fluidically connected to reagent chamber 2110a through a channel 2122a, operates to draw away air and any excess fluid.

Once fluid channels 2114, 2116, and 2118a have been primed with fluid, reservoir pump 2112' transfers a measured amount of fluid into fluid channel 2124 between the reservoir pump and sample chamber 2102, to fill channel 2124, channel 2126a between the sample chamber and reagent chamber 2110a, and channel 2122a between reagent chamber 2110a and waste pump 2120'. Waste pump 2120' operates to draw away air and fluid as channels 2124, 2126a, and 2122a are primed with fluid. Next, reservoir pump 2112' transfers additional fluid through channel 2118a to reagent chamber 2110a, into channel 2130a, through droplet generation region 2132a, and into a multi-port valve 2134' of instrument 2100'.

At this point, the fluid channels leading from reservoir pump 2112' to sample chamber 2102, waste chamber 2104, and reagent chamber 2110a, and from reagent chamber 2110a to multi-port valve 2134', have all been primed with fluid. Reservoir pump 2112' may then be used to prime the fluid channels associated with any additional reagent chambers. For example, reservoir pump 2112' may transfer a measured amount of fluid through channel 2124 to fill channel 2126b between the sample chamber and reagent chamber 2110b, and channel 2122b between reagent chamber 2110b and waste pump 2120', while waste pump 2120' operates to draw away air and fluid. Reservoir pump 2112' then may transfer fluid through channel 2128b directly to reagent chamber 2110b, into channel 2130b, through droplet generation region 2132b, and into multi-port valve 2134'. In a similar manner, reservoir pump 2112' (or in some cases, additional reservoir pumps) can be used to prime the fluid channels associated with any desired number of reagent chambers.

Once the channels of cartridge 2100 have been primed to a desired degree, a sample or sample-containing fluid may be placed in the sample chamber, and all of the previously described steps of purification, concentration, lysing, reagent combination, and/or droplet generation may be performed as described previously with respect to other cartridge embodiments. However, one additional distinction between cartridge 2100 and the previously described cartridges is that cartridge 2100 does not include an oil reservoir to supply oil for droplet generation. Rather, an oil reservoir 2140' is included in instrument 2100'. Oil reservoir 2140' is configured to supply oil through lines 2142a and 2144a to droplet generation region 2132a, and through lines 2142b and 2144b to droplet generation region 2132b. The oil reservoir can be configured to supply oil to any desired number of additional droplet generation regions, corresponding to additional reagent reservoirs beyond the two depicted in FIG. 11. After sample/reagent droplets are generated, they may be transferred to multi-port valve 2134', which is configured to transfer the droplets to a thermocycling portion of instrument 2100' for PCR amplification.

Example F

Disposable Sample Cartridge 4

Figure 12:
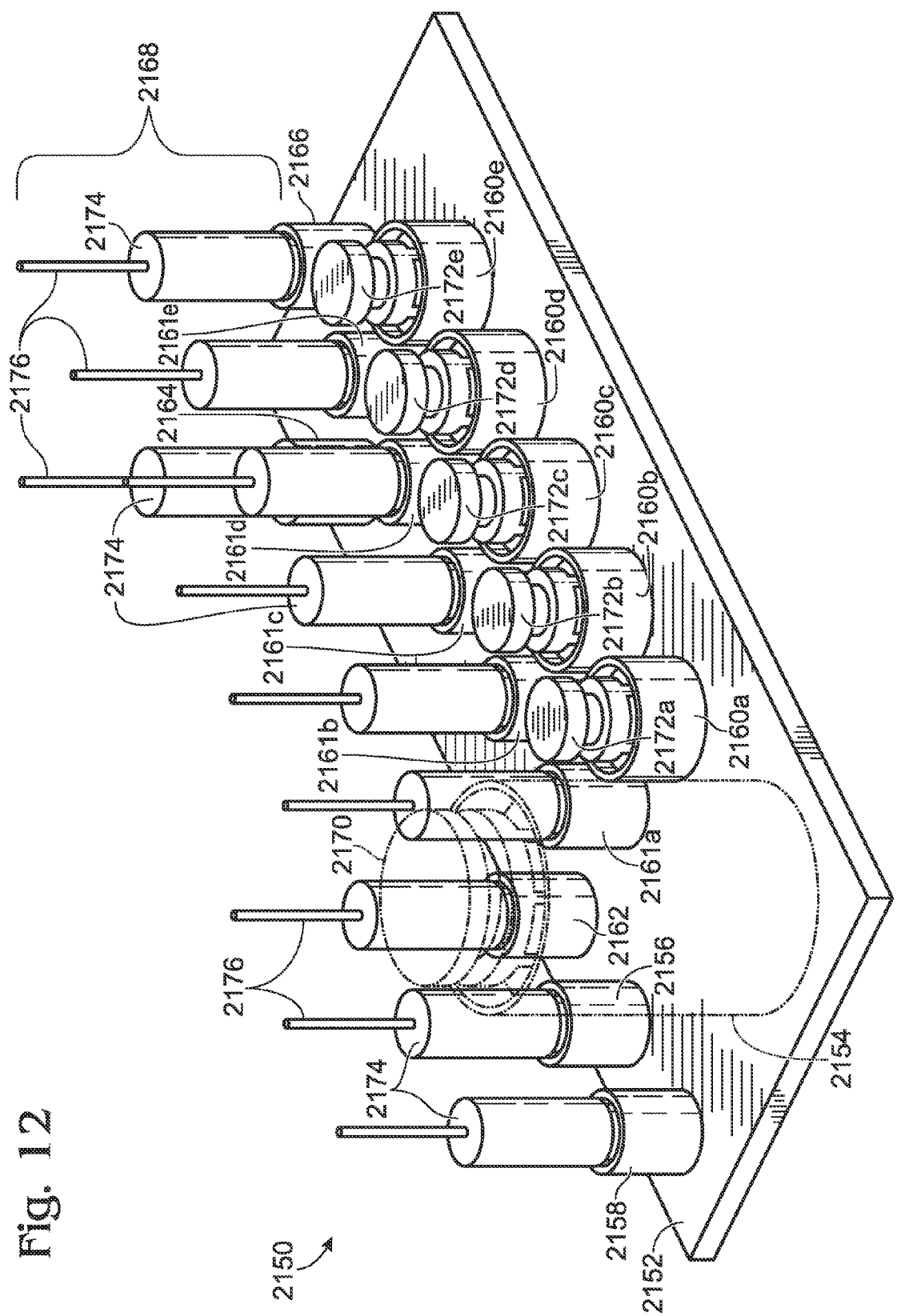
FIG. 12 is an isometric view of still another disposable sample preparation cartridge, in accordance with aspects of the present disclosure.
Figure 13:
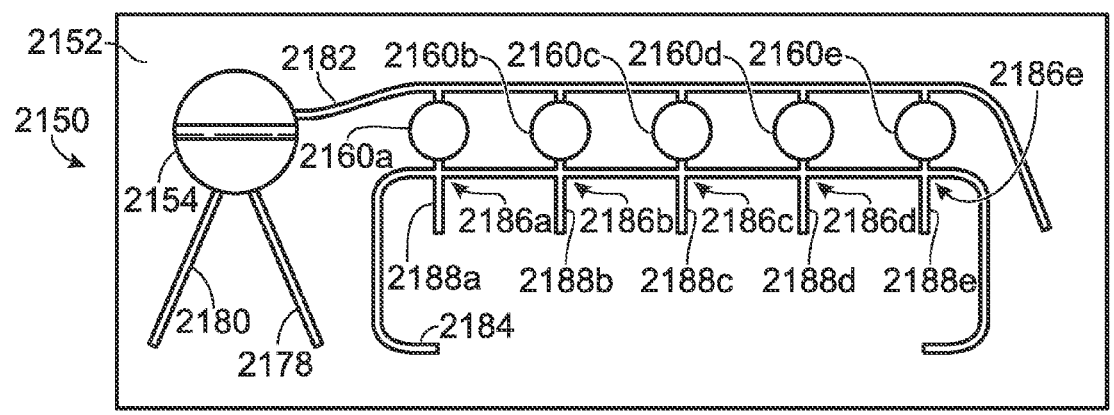
FIG. 13 is a bottom view of the cartridge of FIG. 12.

This example describes aspects of yet another alternative disposable sample preparation cartridge; see FIGS. 12 and 13.

FIG. 12 is an isometric view of an interior portion of the exemplary cartridge, generally indicated at 2150. Cartridge 2150 is configured to interface with an instrument (not shown), so that prepared samples can be transferred to the instrument, generally in the form of a water-in-oil emulsion, for PCR amplification and analysis. In addition to the interior portion depicted in FIG. 12, cartridge 2150 also may include a suitable exterior housing (not shown) disposed around some or the entirety of the interior portion. The exterior housing may be configured to protect the interior portion and may be shaped to facilitate storage and/or transportation of multiple cartridges.

Cartridge 2150 includes an upper body portion 2152, plus various plungers and connectors that will be described in more detail below. Body portion 2152 may be unitarily constructed, for example, by injection molding a thermoplastic or other similar material. A second, lower body portion (not shown) may be included in cartridge 2150 and connected to the upper body portion by heat sealing, gluing, or otherwise fastening the two body portions together, but this lower body portion is simply a flat, featureless sheet of material and therefore will not be described further. Restricting the significant features within a unitarily constructed cartridge body portion, such as upper body portion 2152, may have advantages in cost, simplicity, structural integrity, and/or improved functionality compared to a two-piece construction where both pieces include features used for fluid manipulation and transfer, as shown and described (for example) with reference to FIGS. 3 and 4 above.

Body portion 2152 of cartridge 2150 includes a sample chamber 2154 configured to receive a sample that potentially contains a target nucleic acid sequence, a reservoir chamber 2156 configured to supply a wash and/or a reconstitution solution, a waste chamber 2158 configured to receive waste material, and various reagent chambers 2160a, 2160b, 2160c, 2160d, 2160e configured to receive sample-containing fluid and to combine the sample-containing fluid with a reagent mixture prior to PCR thermocycling. In addition, body portion 2152 of cartridge 2150 includes droplet chambers 2161a, 2161b, 2161c, 2161d, 2161e, each of which is configured to receive an emulsion of water-in-oil, sample-containing droplets including the sample/reagent mixture contained in the corresponding reagent chamber. As described previously, any desired number of reagent chambers (and corresponding droplet chambers) may be included in a cartridge. The sample chamber, reservoir chamber, waste chamber, and reagent chambers are substantially similar in both structure and function to their counterparts in cartridge 1720 of FIG. 3, including any appropriate filters, stirring elements, and the like, and accordingly will not be described in detail again.

Body portion 2152 also includes an oil input chamber 2162, an oil outlet chamber 2164, and a primer outlet chamber 2166. Oil input chamber 2162 is configured to hold and transfer oil that will be used to produce sample-containing droplets in a water-in-oil emulsion, in a manner described below in more detail. Oil outlet chamber 2164 is configured to receive oil that has been transferred out of the oil input chamber, but that has not been utilized in the water-in-oil emulsion of sample-containing droplets. The excess oil received in oil outlet chamber 2164 may be either discarded or recycled (i.e., redirected to the oil input chamber). Primer outlet chamber 2166 is configured to receive one or more priming fluids during an initial cartridge priming step, in a manner that will be described in more detail below.

In addition to upper body portion 2152, cartridge 2150 also includes a fluid manipulation portion, generally indicated at 2168. The fluid manipulation portion of the cartridge includes a sample chamber plunger 2170 and various reagent chamber plungers 2172a, 2172b, 2172c, 2172d, 2172e. The plungers are configured to move up and down within their respective chambers, to cause fluid to be transferred into and out of the chambers in a desired fashion. Fluid manipulation portion 2168 of the cartridge also includes a plurality of substantially similar capillary connectors 2174, and a plurality of substantially similar capillaries 2176. The capillary connectors are configured to transfer fluid to and/or from the corresponding chamber to the corresponding capillary, which is configured to interface with an associated thermocycling instrument.

FIG. 13 is a bottom view of upper body portion 2152, illustrating the fluid connections between various portions of the cartridge. As noted above, a lower body portion (not shown) of cartridge 2150 will generally be disposed flush against the bottom surface of upper body portion 2152, to form a fluid tight seal so that fluid is only able to travel between portions of the cartridge through the various fluid channels shown in FIG. 13. Specifically, a fluid channel 2178 is configured to transfer reconstitution/wash and/or priming fluid into sample chamber 2154 from reservoir chamber 2156, and another fluid channel 2180 is configured to transfer waste fluid out of sample chamber 2154 and into waste chamber 2158. Yet another fluid channel 2182 is configured to transfer sample-containing fluid from sample chamber 2154 into reagent chambers 2160a, 2160b, 2160c, 2160d, 2160e, and also to transfer priming fluid from sample chamber 2154 into primer outlet chamber 2166. Yet another fluid channel 2184 is configured to transfer oil from oil input chamber 2162 to a plurality of droplet generation regions 2186a, 2186b, 2186c, 2186d, 2186e, where the oil is combined with sample/reagent mixture fluid from the reagent chambers to form water-in-oil droplets. A plurality of fluid channels 2188a, 2188b, 2188c, 2188d, 2188e are configured to transport the generated droplets from their respective droplet generation regions to corresponding droplet chambers 2161a, 2161b, 2161c, 2161d, 2161.

Typically, cartridge 2150 will be primed with fluid(s) supplied by a related instrument. For instance, when a fluid connection has been established between the cartridge and the instrument, priming fluid such as oil, water, or any other substantially incompressible fluid may be transferred from the instrument, through the appropriate capillary and capillary connector, and into reservoir chamber 2156. The priming fluid then may be transferred from the reservoir chamber, through fluid channel 2178, and into sample chamber 2154. From the sample chamber, the priming fluid may be transferred through fluid channel 2182 and into primer outlet chamber 2166 and/or the reagent chambers. Similarly, oil or some other priming fluid may be transferred from the instrument into oil input chamber 2162, through fluid channel 2184, and into oil outlet chamber 2164 and/or the droplet generation chambers. In this manner, desired priming fluids can be used to prime any desired subset of the fluid chambers and channels of cartridge 2150.

Plungers 2170, 2172a, 2172b, 2172c, 2172d, and 2172e (and any other plungers contemplated by the present disclosure) each may be configured both to direct fluids as desired through particular fluid channels, and also to selectively allow or prevent fluid flow in and out of various chambers. In other words, each plunger may be configured to operate as a valve in addition to operating as a plunger, by selectively opening or closing the entrance to one or more particular fluid channels. For example, when reagent plungers 2172a, 2172b, 2172c, 2172d, and 2172e are in their most downward positions (minimizing the volumes of the reagent chambers), the plungers may be configured to block fluid connection between fluid channel 2182 and fluid channel 2184 (see FIG. 13), so that channel 2182 can be primed with fluid independently of channel 2184. In a similar manner, the plungers of any cartridge can be used as valves, to prevent or allow fluid flow between various portions of the cartridge.

Disposable cartridge 2150 of FIGS. 12 and 13 is just one example of a disposable cartridge that is configured to be primed with fluid supplied by an associated instrument. The present disclosure contemplates other disposable cartridges that may be substantially similar except for the disposition of various chambers and/or variations in how fluids are routed between the various chambers, or between the chambers and the instrument. For example, the waste chamber and/or the reservoir chamber may be disposed on the instrument rather than on the cartridge as in FIGS. 12 and 13. A plurality of oil input chambers may be provided, with each chamber supplying oil to a single droplet generation region rather than one chamber supplying oil to multiple regions as in FIGS. 12 and 13. The droplet generation regions may take any of the various forms described previously with respect to FIGS. 8A-8F, such as a cross configuration instead of a single T configuration as in FIGS. 12 and 13. Excess oil or priming fluid may either be discarded as in FIGS. 12 and 13, recycled, or routed through the droplet generator outlet(s). Droplets may be routed either through multiple outlets as in FIGS. 12 and 13 or through a single, common outlet. Virtually any combination of the above variations may be adopted, resulting in a modified system that may be most appropriate for a particular application.

The present systems may be combined, optionally, with apparatus, methods, compositions, and/or kits, or components thereof, described in the references listed above under Cross-References and incorporated herein by reference.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

The invention claimed is:

1. A method of nucleic acid amplification, comprising:
purifying a fluid sample in a portion of a disposable, single-use cartridge;
lysing the sample in a portion of the cartridge;
combining the purified, lysed sample with a reagent mixture in a portion of the cartridge;
driving flow of at least one carrier fluid stream and a sample stream to a channel intersection at which droplets containing the sample are generated to form an emulsion, wherein the sample stream includes the purified, lysed sample combined with the reagent mixture; and
cycling the emulsion thermally in a thermocycling instrument to which the emulsion is transferred from the cartridge,
wherein the step of combining includes a step of advancing a first plunger that is operatively connected to a first reservoir containing one of the sample and the reagent mixture, while retracting a second plunger that is operatively connected to a second reservoir containing the other of the sample and the reagent mixture, to move fluid out of the first reservoir and into the second reservoir.

2. The method of claim 1, wherein the step of purifying includes a step of extracting the sample from a sample collector within the cartridge.

3. The method of claim 1, wherein the step of purifying includes a step of concentrating the sample within the cartridge.

4. The method of claim 1, wherein the step of purifying includes a step of separating sample components based on size before the step of lysing.

5. The method of claim 1, wherein the step of purifying includes a step of separating nucleic acids from other sample components after the step of lysing.

6. The method of claim 1, wherein the step of lysing includes a step of agitating the sample mechanically.

7. The method of claim 6, wherein the step of agitating the sample mechanically includes a step of applying magnetic force to a stir element.

8. The method of claim 1, where the step of cycling includes a step of driving flow of the emulsion along a channel that extends through a plurality of temperature zones.

9. The method of claim 1, wherein the step of cycling includes a step of holding the emulsion in a container while a temperature of the container is changed over time.

10. The method of claim 1, wherein the cartridge is a first cartridge, wherein the steps of purifying, lysing, combining, and driving are performed with the first cartridge operatively connected to an instrument that controls the steps of purifying, lysing, combining, and driving, further comprising a step of disconnecting the first cartridge and a step of repeating the steps of purifying, lysing, combining, and driving within a second cartridge operatively connected to the instrument after the first cartridge is disconnected.

11. The method of claim 10, wherein the instrument supplies fluid to the first and second cartridges during at least one of the steps of purifying, lysing, combining, and driving within each cartridge.

12. The method of claim 11, wherein the instrument supplies a continuous phase for the emulsion.

13. The method of claim 10, wherein the instrument performs the step of cycling the emulsion thermally.

14. The method of claim 1, further comprising a step of providing a cartridge including
a sample chamber configured to receive a sample,
one or more reagent chambers each fluidically connected to the sample chamber and each configured to receive sample-containing fluid from the sample chamber and to combine the sample-containing fluid with a reagent mixture, and
one or more droplet generation regions, each including a channel intersection at which droplets containing the sample are generated to form an emulsion and each fluidically connected to one of the reagent chambers and each configured to receive sample/reagent mixture fluid from one of the reagent chambers and to combine the sample/reagent mixture fluid with a continuous phase to form an emulsion of sample-containing droplets, and
wherein the cartridge is configured to be connected to a reusable instrument that drives operation of the cartridge.

15. The method of claim 14, wherein the step of providing includes a step of providing a cartridge including a reservoir chamber fluidically connected to the sample chamber and configured to supply a reconstitution fluid to the sample chamber.

16. The method of claim 14, wherein the step of providing includes a step of providing a cartridge in which the one or more reagent chambers are a plurality of reagent chambers.

17. The method of claim 14, wherein the step of providing includes a step of providing a cartridge in which the one or more droplet generation regions are a plurality of droplet generation regions.

18. The method of claim 14, wherein the step of providing includes a step of providing a cartridge in which the sample chamber, the reagent chambers, and the droplet generation regions are fluidically connected to each other by fluid channels defined collectively by a first body portion and a second body portion that are attached to each other, and wherein the fluid channels are created by grooves that are formed in a surface of the first body portion and that are covered by a substantially planar surface of the second body portion.

19. The method of claim 14, wherein the step of providing includes a step of providing a cartridge including an input chamber configured to receive a continuous phase to be transferred to the droplet generation regions.

20. The method of claim 19, wherein the step of providing includes a step of providing a cartridge including an outlet chamber configured to receive a portion of the continuous phase that has been transferred out of the input chamber, but that has not been utilized in one of the emulsions.

21. The method of claim 14, wherein the step of providing includes a step of providing a cartridge including a plurality of droplet chambers each configured to receive one of the generated emulsions.

22. The method of claim 14, wherein the step of providing includes a step of providing a cartridge including a plurality of plungers configured to be moved to transfer fluid into and out of the chambers.

23. The method of claim 22, wherein the step of providing includes a step of providing a cartridge in which each plunger is configured to act as a valve by selectively closing an entrance to at least one fluid channel when such plunger is in its most advanced position.

24. The method of claim 14, wherein the step of providing includes a step of providing a cartridge in which a plurality of connectors carry fluid between at least one chamber of the cartridge and the instrument.

25. The method of claim 14, wherein the step of providing includes a step of providing a cartridge in which the sample chamber includes an agitation element configured to be agitated by magnetic forces.

26. The method of claim 14, wherein the step of providing includes a step of providing a cartridge in which the one or more reagent chambers include a plurality of reagent chambers that are fluidically connected to the sample chamber in parallel.

27. The method of claim 14, wherein the continuous phase includes oil, wherein the step of providing includes a step of providing a cartridge in which the cartridge further comprises at least one oil reservoir fluidically connected to at least one of the reagent chambers and configured to supply the oil used to form a corresponding emulsion.

28. The method of claim 27, wherein the step of providing includes a step of providing a cartridge in which the one or more reagent chambers are a plurality of reagent chambers and in which the at least one oil reservoir includes a distinct oil reservoir for each reagent chamber and configured to supply the oil used to form the corresponding emulsion.

29. The method of claim 14, wherein the step of providing includes a step of providing a cartridge in which at least one of the reagent chambers has been pre-loaded with reagents.

30. The method of claim 29, wherein the step of providing includes a step of providing a cartridge in which at least one of the reagent chambers has been pre-loaded with primers for amplification of a nucleic acid target.

31. The method of claim 18, wherein the step of providing includes a step of providing a cartridge in which the droplet generation regions are defined collectively by the surface of the first body portion and the substantially planar surface of the second body portion.

32. The method of claim 1, wherein a same amount of fluid moves out of the first reservoir and moves into the second reservoir during the step of advancing.

33. The method of claim 1, wherein a third plunger is operatively connected to a third reservoir, and wherein the second plunger and the third plunger are retracted during the step of advancing.

* * * * *